US012304962B2

(12) United States Patent
Spanholtz et al.

(10) Patent No.: US 12,304,962 B2
(45) Date of Patent: May 20, 2025

(54) CAR NK CELLS

(71) Applicant: GLYCOSTEM THERAPEUTICS B.V., AB Oss (NL)

(72) Inventors: Jan Spanholtz, AB Oss (NL); Nina Kok, AB Oss (NL); Alessandra Gatti, Milan (IT); Giuliana Vallanti, Milan (IT); Catia Traversari, Milan (IT)

(73) Assignee: GLYCOSTEM THERAPEUTICS B.V., AB Oss (NL)

( * ) Notice: Subject to any disclaimer, the term of this patent is extended or adjusted under 35 U.S.C. 154(b) by 1149 days.

(21) Appl. No.: 17/059,059

(22) PCT Filed: May 29, 2019

(86) PCT No.: PCT/EP2019/063920
§ 371 (c)(1),
(2) Date: Nov. 25, 2020

(87) PCT Pub. No.: WO2019/229109
PCT Pub. Date: Dec. 5, 2019

(65) Prior Publication Data
US 2022/0064599 A1  Mar. 3, 2022

(30) Foreign Application Priority Data
May 30, 2018 (EP) .................................. 18175055

(51) Int. Cl.
| C07K 16/28 | (2006.01) |
| A61K 40/15 | (2025.01) |
| A61K 40/31 | (2025.01) |
| A61K 40/42 | (2025.01) |
| C07K 14/705 | (2006.01) |
| C07K 14/725 | (2006.01) |
| C12N 5/00 | (2006.01) |
| C12N 5/0783 | (2010.01) |
| C12N 5/0789 | (2010.01) |
| C12N 15/86 | (2006.01) |
| G01N 33/50 | (2006.01) |
| G01N 33/543 | (2006.01) |

(52) U.S. Cl.
CPC .......... *C07K 16/2884* (2013.01); *A61K 40/15* (2025.01); *A61K 40/31* (2025.01); *A61K 40/421* (2025.01); *C07K 14/7051* (2013.01); *C07K 14/70521* (2013.01); *C12N 5/0087* (2013.01); *C12N 5/0646* (2013.01); *C12N 5/0647* (2013.01); *C12N 15/86* (2013.01); *G01N 33/5002* (2013.01); *G01N 33/54326* (2013.01); *A61K 2239/38* (2023.05); *A61K 2239/48* (2023.05); *C07K 2317/622* (2013.01); *C07K 2319/03* (2013.01); *C12N 2501/125* (2013.01); *C12N 2501/145* (2013.01); *C12N 2501/22* (2013.01); *C12N 2501/2302* (2013.01); *C12N 2501/2306* (2013.01); *C12N 2501/2307* (2013.01); *C12N 2501/2315* (2013.01); *C12N 2501/26* (2013.01); *C12N 2740/15043* (2013.01)

(58) Field of Classification Search
CPC .............. A61K 40/15; C12N 2501/125; C12N 2501/145; C12N 2501/22
See application file for complete search history.

(56) References Cited

U.S. PATENT DOCUMENTS

| 2014/0322183 A1 | 10/2014 | Milone et al. |
| 2015/0010583 A1 | 1/2015 | Spanholtz |
| 2015/0225697 A1 | 8/2015 | Law et al. |
| 2016/0250258 A1 | 9/2016 | Delaney et al. |
| 2016/0361360 A1 | 12/2016 | Chang et al. |
| 2017/0137783 A1 | 5/2017 | Bedoya et al. |
| 2017/0204372 A1 | 7/2017 | Mohler et al. |
| 2017/0247428 A1 | 8/2017 | Bondanza et al. |
| 2017/0355957 A1 | 12/2017 | Biondi et al. |
| 2018/0008637 A1 | 1/2018 | Murphy et al. |
| 2018/0057795 A1 | 3/2018 | Childs et al. |

FOREIGN PATENT DOCUMENTS

| KR | 20160079854 A | 7/2016 |
| KR | 20170098938 A | 8/2017 |
| WO | 2005123912 A2 | 12/2005 |
| WO | 2016/042461 A1 | 3/2016 |

OTHER PUBLICATIONS

Shevtsov (2016, Front. Immunol. 7:9 pages.*
Yadav (International Journal of Stem Cells 2020;13:326-334).*
Zhang (Curr Opin Hematol. Jul. 2008 ; 15(4): 307-311).*
Satiro Nakamura De Oliveira et al., Modification of Hematopoietic Stem/Progenitor Cells with CD19-Specific Chimeric Antigen Receptors as a Novel Approach for Cancer Immunotherapy, Human Gene Therapy 24:824-839 (Oct. 2013) © Mary Ann Liebert, Inc, Research Articles, pp. 824-839.
Mario Amendola et al., Coordinate dual-gene transgenesis by lentiviral vectors carrying synthetic bidirectional promoters, Nature Biotechnology, vol. 23, No. 1, pp. 108-116 (2005).
A. Hombach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response, Gene Therapy, vol. 17, pp. 1206-1213 (2010).

(Continued)

*Primary Examiner* — Valerie E Bertoglio
(74) *Attorney, Agent, or Firm* — Brooks Kushman P.C.

(57) ABSTRACT

A method of manufacturing of Natural Killer (NK) Cells genetically modified with lentiviral vectors carrying a polynucleotide coding for a Chimeric Antigen Receptors (CARs). CAR-NK cells obtained with the method, and the use of the CAR-NK cells in medicine, in particular for use in a method of treating cancer is also disclosed.

12 Claims, 5 Drawing Sheets
Specification includes a Sequence Listing.

(56) References Cited

OTHER PUBLICATIONS

Jan Spanholtz et al., High log-scale expansion of functional human natural killer cells from umbilical cord blood CD34-positive cells for adoptive cancer immunotherapy, PLoS One, vol. 5, Issue 2, e9221, Feb. 15, 2010.

Monica Casucci et al., CD44v6-targeted T cells mediate potent antitumor effects against acute myeloid leukemia and multiple myeloma, Blood, vol. 122, Issue 20, pp. 3461-3472, Nov. 14, 2013.

Zhena Ni et al., Expression of chimeric receptor CD4ζ by natural killer cells derived from human pluripotent stem cells improves in vitro activity but does not enhance suppression of HIV infection in vivo, Stem Cells, vol. 32, Issue 4, pp. 1021-1031, Apr. 2014.

Emily Lowe et al., In Vitro Generation of Human NK Cells Expressing Chimeric Antigen Receptor Through Differentiation of Gene-Modified Hematopoietic Stem Cells, Methods Mol Biol., 2016, 1441:241-251.

Beatriz Martin-Antonio et al., Natural Killer Cells: Angels and Devils for Immunotherapy, International Journal of Molecular Science, 2017, vol. 18, Issue 9, 1868. Published Aug. 29, 2017.

Katayoun Rezvani et al., Engineering Natural Killer Cells for Cancer Immunotherapy, Molecular Therapy, 2017, vol. 25, Issue 8, pp. 1769-1781.

Monica Casucci et al., Extracellular NGFR Spacers Allow Efficient Tracking and Enrichment of Fully Functional CAR-T Cells Co-Expressing a Suicide Gene, Frontiers in Immunology, 2018, vol. 9, Article 507, Published Mar. 21, 2018.

V. Leuci et al., CD44v6 as innovative sarcoma target for CAR-redirected CIK cells, Oncoimmunology, 2018, vol. 7, Issue 5, e1423167, Published Feb. 15, 2018.

International Search Report for PCT/EP2019/063920, Prepared by the European Patent Office, Mailing date Jul. 24, 2019, 3 pages.

Korean Office Action for Application No. 10-2020-7037462, Dispatch date Sep. 30, 2024, 14 pages including English Translation.

\* cited by examiner

A Cytotoxicity (%) end of culture

| Targets | B non T | B T | A non T | A T |
|---|---|---|---|---|
| K562 | 68.41 | 53.23 | 60.61 | 34.12 |
| THP-1 monocytes | 24.83 | 27.77 | 27.41 | 24.43 |
| THP-1 macrophages | 14.58 | 14.26 | 17.11 | 9.79 |
| T98G | 40.64 | 48.15 | 47.11 | 38.34 |

B Cytotoxicity (%) after reconstitution

| Targets | B non T | B T | A non T | A T |
|---|---|---|---|---|
| K562 | 72.37 | 65.65 | 72.86 | 36.04 |

C Degranulation (%) after reconstitution

| Targets | B non T | B T | A non T | A T |
|---|---|---|---|---|
| K562 | 26.47 | 31.42 | 27.68 | 20.18 |

| Culture day 31 | A non T | A T |
|---|---|---|
| CD56+ cells % gated | 61.92 | 71.17 |
| panKIR % gated on CD56+ cells | 4.99 | 8.54 |
| DNAM-1 % gated on CD56+ cells | 59.09 | 28.86 |
| NKG2A % gated on CD56+ cells | 58.51 | 64.36 |
| NKG2C % gated on CD56+ cells | 4.86 | 2.83 |
| NKG2D % gated on CD56+ cells | 84.03 | 73.33 |
| CD16 % gated on CD56+ cells | 9.24 | 14.40 |

B

| After reconstitution | B non T | B T | A non T | A T |
|---|---|---|---|---|
| CD56+ cells % gated | 98.07 | 98.76 | 97.38 | 98.47 |
| DNAM-1 % gated on CD56+ cells | 75.73 | 66.63 | 62.38 | 30.6 |
| NKG2A % gated on CD56+ cells | 42.65 | 47.07 | 34.56 | 53.56 |
| NKG2C % gated on CD56+ cells | 2.31 | 1.88 | 2.16 | 1.23 |
| NKG2D % gated on CD56+ cells | 71.84 | 69.39 | 71.08 | 42.58 |
| CD16 % gated on CD56+ cells | 4.61 | 5.64 | 4.08 | 7.34 |
| KIR2DL2/L3+/NGFR+ gated on CD56+ | 0.36 | 2.57 | 0.33 | 6.85 |
| KIR2DL2/L3-/NGFR+ gated on CD56+ | 0.70 | 28.62 | 0.91 | 71.45 |
| KIR2DL2/L3+ gated on CD56+ cells | 3.00 | 5.66 | 3.16 | 7.75 |
| KIR3DL+ gated on CD56+ cells | N.A. | N.A. | 0.25 | 0.88 |
| KIR2DL1+ gated on CD56+ cells | 0.50 | 0.81 | 0.78 | 1.90 |

Figure 5

SEQUENCE LISTING

<160> NUMBER OF SEQ ID NOS: 14

<210> SEQ ID NO 1
<211> LENGTH: 222
<212> TYPE: PRT
<213> ORGANISM: Artificial Sequence
<220> FEATURE:
<223> OTHER INFORMATION: Protein sequence spacer domain (NWL)

<400> SEQUENCE: 1

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val

```
              35                  40                  45
Val Ser Ala Thr Glu Pro Cys Lys Pro Cys Thr Glu Cys Val Gly Leu
        50                  55                  60
Gln Ser Met Ser Ala Pro Cys Val Glu Ala Asp Asp Ala Val Cys Arg
 65                  70                  75                  80
Cys Ala Tyr Gly Tyr Tyr Gln Asp Glu Thr Thr Gly Arg Cys Glu Ala
                 85                  90                  95
Cys Arg Val Cys Glu Ala Gly Ser Gly Leu Val Phe Ser Cys Gln Asp
            100                 105                 110
Lys Gln Asn Thr Val Cys Glu Glu Cys Pro Asp Gly Thr Tyr Ser Asp
                115                 120                 125
Glu Ala Asn His Val Asp Pro Cys Leu Pro Cys Thr Val Cys Glu Asp
            130                 135                 140
Thr Glu Arg Gln Leu Arg Glu Cys Thr Arg Trp Ala Asp Ala Glu Cys
145                 150                 155                 160
Glu Glu Ile Pro Gly Arg Trp Ile Thr Arg Ser Thr Pro Pro Glu Gly
                165                 170                 175
Ser Asp Ser Thr Ala Pro Ser Thr Gln Glu Pro Glu Ala Pro Pro Glu
            180                 185                 190
Gln Asp Leu Ile Ala Ser Thr Val Ala Gly Val Val Thr Thr Val Met
                195                 200                 205
Gly Ser Ser Gln Pro Val Val Thr Arg Gly Thr Thr Asp Asn
            210                 215                 220

<210> SEQ ID NO 2
<211> LENGTH: 666
<212> TYPE: DNA
<213> ORGANISM: Artificial Sequence
<220> FEATURE:
<223> OTHER INFORMATION: Nucleotide sequence spacer domain (NWL)

<400> SEQUENCE: 2
aaagaggcct gccccaccgg cctgtacacc cacagcggag agtgctgcaa ggcctgcaac      60
ctgggagagg gcgtggccca gccttgcggc gccaatcaga ccgtgtgcga gccctgcctg     120
gacagcgtga ccttcagcga cgtggtgtcc gccaccgagc cctgcaagcc ttgcaccgag     180
tgtgtgggcc tgcagagcat gagcgccccc tgcgtggaag ccgacgacgc cgtgtgtaga     240
tgcgcctacg gctactacca ggacgagaca accggcagat gcgaggcctg tagagtgtgc     300
gaggccggca gcggcctggt gttcagttgt caagacaagc agaataccgt gtgtgaagag     360
tgccccgacg gcacctacag cgacgaggcc aaccacgtgg accctgcct gccctgcact      420
gtgtgcgagg acaccgagcg gcagctgcgc gagtgcacaa gatgggccga cgccgagtgc     480
gaagagatcc ccggcagatg gatcaccaga agcacccccc ctgagggcag cgacagcacc     540
gcccctagca cccaggaacc tgaggcccct cccgagcagg acctgatcgc ctctacagtg     600
gccggcgtgg tgacaaccgt gatgggcagc tctcagcccg tggtgacacg gggcaccacc     660
gacaat                                                                 666

<210> SEQ ID NO 3
<211> LENGTH: 162
<212> TYPE: PRT
<213> ORGANISM: Artificial Sequence
<220> FEATURE:
<223> OTHER INFORMATION: Protein sequence spacer domain (NWS)

<400> SEQUENCE: 3
```

```
Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
            35                  40                  45

Val Ser Ala Thr Glu Pro Cys Lys Pro Cys Thr Glu Cys Val Gly Leu
        50                  55                  60

Gln Ser Met Ser Ala Pro Cys Val Glu Ala Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
                100                 105                 110

Lys Gln Asn Thr Val Cys Glu Cys Pro Asp Gly Thr Tyr Ser Asp
            115                 120                 125

Glu Ala Asn His Val Asp Pro Cys Leu Pro Cys Thr Val Cys Glu Asp
        130                 135                 140

Thr Glu Arg Gln Leu Arg Glu Cys Thr Arg Trp Ala Asp Ala Glu Cys
145                 150                 155                 160

Glu Glu

<210> SEQ ID NO 4
<211> LENGTH: 486
<212> TYPE: DNA
<213> ORGANISM: Artificial sequence
<220> FEATURE:
<223> OTHER INFORMATION: Nucleotide sequence spacer domain (NWS)

<400> SEQUENCE: 4
aaagaggcct gccccaccgg cctgtacacc cacagcggag agtgctgcaa ggcctgcaac      60
ctgggagagg gcgtggccca gccttgcggc gccaatcaga ccgtgtgcga gccctgcctg     120
gacagcgtga ccttcagcga cgtggtgtcc gccaccgagc cctgcaagcc ttgcaccgag     180
tgtgtgggcc tgcagagcat gagcgccccc tgcgtggaag ccgacgacgc cgtgtgtaga     240
tgcgcctacg gctactacca ggacgagaca accggcagat gcgaggcctg tagagtgtgc     300
gaggccggca gcggcctggt gttcagttgt caggacaagc agaacaccgt gtgtgaagag     360
tgccccgacg gcacctacag cgacgaggcc aaccacgtgg acccctgcct gccctgcact     420
gtgtgcgagg acaccgagcg gcagctgcgc gagtgcacaa gatgggccga cgccgagtgc     480
gaggaa                                                                486

<210> SEQ ID NO 5
<211> LENGTH: 200
<212> TYPE: PRT
<213> ORGANISM: Artificial sequence
<220> FEATURE:
<223> OTHER INFORMATION: Protein sequence spacer domain (NML)

<400> SEQUENCE: 5

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
            35                  40                  45
```

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Cys Pro Asp Gly Thr Tyr Ser Asp
        115                 120                 125

Glu Ala Ala Arg Ala Ala Asp Ala Glu Cys Glu Ile Pro Gly Arg
    130                 135                 140

Trp Ile Thr Arg Ser Thr Pro Pro Glu Gly Ser Asp Ser Thr Ala Pro
145                 150                 155                 160

Ser Thr Gln Glu Pro Glu Ala Pro Pro Glu Gln Asp Leu Ile Ala Ser
                165                 170                 175

Thr Val Ala Gly Val Val Thr Thr Val Met Gly Ser Ser Gln Pro Val
            180                 185                 190

Val Thr Arg Gly Thr Thr Asp Asn
        195                 200

<210> SEQ ID NO 6
<211> LENGTH: 600
<212> TYPE: DNA
<213> ORGANISM: Artificial sequence
<220> FEATURE:
<223> OTHER INFORMATION: Nucleotide sequence spacer domain (NML)

<400> SEQUENCE: 6
aaagaggcct gccccaccgg cctgtacacc cacagcggag agtgctgcaa ggcctgcaac    60
ctgggagagg gcgtggccca gccttgcggc gccaatcaga ccgtgtgcga gccctgcctg   120
gacagcgtga ccttcagcga cgtggtgtcc gccaccgagc cctgcaagcc ttgcaccgag   180
tgtgtgggcc tgcagagcat gagcgccccc tgcgtggaag ccgacgacgc cgtgtgtaga   240
tgcgcctacg gctactacca ggacgagaca accggcagat gcgaggcctg tagagtgtgc   300
gaggccggca gcggcctggt gttcagttgt caagacaagc agaataccgt gtgtgaagag   360
tgccccgacg gcacctacag cgacgaagcc gccagagccg ccgacgccga gtgcgaagag   420
atccccggca gatggatcac cagaagcacc cccctgagg gcagcgacag caccgcccct   480
agcacccagg aacctgaggc ccctcccgag caggacctga tcgcctctac agtggccggc   540
gtggtgacaa ccgtgatggg cagctctcag cccgtggtga cacggggcac caccgacaat   600

<210> SEQ ID NO 7
<211> LENGTH: 140
<212> TYPE: PRT
<213> ORGANISM: Artificial Sequence
<220> FEATURE:
<223> OTHER INFORMATION: Protein sequence spacer domain (NMS)

<400> SEQUENCE: 7

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

```
Val Ser Ala Thr Glu Pro Cys Lys Pro Cys Thr Cys Val Gly Leu
 50                  55                  60

Gln Ser Met Ser Ala Pro Cys Val Glu Ala Asp Asp Ala Val Cys Arg
 65                  70                  75                  80

Cys Ala Tyr Gly Tyr Tyr Gln Asp Glu Thr Thr Gly Arg Cys Glu Ala
                 85                  90                  95

Cys Arg Val Cys Glu Ala Gly Ser Gly Leu Val Phe Ser Cys Gln Asp
            100                 105                 110

Lys Gln Asn Thr Val Cys Glu Cys Pro Asp Gly Thr Tyr Ser Asp
            115                 120                 125

Glu Ala Ala Arg Ala Ala Asp Ala Glu Cys Glu Glu
130                 135                 140

<210> SEQ ID NO 8
<211> LENGTH: 420
<212> TYPE: DNA
<213> ORGANISM: Artificial Sequence
<220> FEATURE:
<223> OTHER INFORMATION: Nucleotide sequence spacer domain (NMS)

<400> SEQUENCE: 8
aaagaggcct gccccaccgg cctgtacacc cacagcggag agtgctgcaa ggcctgcaac    60
ctgggagagg gcgtggccca gccttgcggc gccaatcaga ccgtgtgcga gccctgcctg   120
gacagcgtga ccttcagcga cgtggtgtcc gccaccgagc cctgcaagcc ttgcaccgag   180
tgtgtgggcc tgcagagcat gagcgccccc tgcgtggaag ccgacgacgc cgtgtgtaga   240
tgcgcctacg gctactacca ggacgagaca accggcagat gcgaggcctg tagagtgtgc   300
gaggccggca gcggcctggt gttcagttgt caggacaagc agaacaccgt gtgtgaagag   360
tgccccgacg gcacctacag cgacgaggcc gcccgggccg ccgacgccga gtgcgaggaa   420

<210> SEQ ID NO 9
<211> LENGTH: 27
<212> TYPE: PRT
<213> ORGANISM: Artificial Sequence
<220> FEATURE:
<223> OTHER INFORMATION: Protein sequence transmembrane domain of CD28

<400> SEQUENCE: 9

Phe Trp Val Leu Val Val Val Gly Gly Val Leu Ala Cys Tyr Ser Leu
 1               5                   10                  15

Leu Val Thr Val Ala Phe Ile Ile Phe Trp Val
                20                  25

<210> SEQ ID NO 10
<211> LENGTH: 68
<212> TYPE: PRT
<213> ORGANISM: Artificial Sequence
<220> FEATURE:
<223> OTHER INFORMATION: Protein sequence transmembrane and
      intracellular portion of the human CD28

<400> SEQUENCE: 10

Phe Trp Val Leu Val Val Val Gly Gly Val Leu Ala Cys Tyr Ser Leu
 1               5                   10                  15

Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
                35                  40                  45

Pro Thr Arg Lys His Tyr Gln Pro Tyr Ala Pro Pro Arg Asp Phe Ala
```

Ala Tyr Arg Ser
65

<210> SEQ ID NO 11
<211> LENGTH: 41
<212> TYPE: PRT
<213> ORGANISM: Artificial Sequence
<220> FEATURE:
<223> OTHER INFORMATION: Protein sequence intracellular domain of CD28

<400> SEQUENCE: 11

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 113
<212> TYPE: PRT
<213> ORGANISM: Artificial Sequence
<220> FEATURE:
<223> OTHER INFORMATION: Protein sequence signaling domain of human CD3
      zeta chain

<400> SEQUENCE: 12

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 13
<211> LENGTH: 1131
<212> TYPE: DNA
<213> ORGANISM: Artificial Sequence
<220> FEATURE:
<223> OTHER INFORMATION: Nucleotide sequence suicide gene is the HSV-TK
      Mut2

<400> SEQUENCE: 13
atggcttcgt accctgcca tcaacacgcg tctgcgttcg accaggctgc gcgttctcgc      60
ggccatagca accgacgtac ggcgttgcgc cctcgccggc agcaagaagc cacggaagtc     120
cgcctggagc agaaaatgcc cacgctactg cgggtttata tagacggtcc tcacgggatg    180
gggaaaacca ccaccacgca actgctggtg gccctgggtt cgcgcgacga tatcgtctac    240
gtacccgagc cgatgactta ctggcaggtg ctgggggctt ccgagacaat cgcgaacatc    300

-continued

```
tacaccacac aacaccgcct cgaccagggc gagatatcgg ccggggacgc ggcggtggta    360
atgacaagcg cccagataac aatgggcatg ccttatgccg tgaccgacgc cgttctggct    420
cctcatgtcg ggggggaggc tgggagttca catgccccgc ccccggccct caccctcatc    480
ttcgaccgcc atcccatcgc cgccctcctg tgctacccgg ccgcgcgata ccttatgggc    540
agcatgaccc cccaggccgt gctggcgttc gtggccctca tcccgccgac cttgcccggc    600
acaaacatcg tgttgggggc ccttccggag gacagacaca tcgaccgcct ggccaaacgc    660
cagcgccccg gcgagcggct tgacctggct atgctggccg cgattcgccg cgtttacggg    720
ctgcttgcca atacggtgcg gtatctgcag ggcggcgggt cgtggtggga ggattgggga    780
cagctttcgg ggacggccgt gccgccccag ggtgccgagc cccagagcaa cgcgggccca    840 cgacccata tcggggacac gttatttacc ctgtttcggg ccccgagtt gctgccccc     900 aacggcgacc tgtataacgt gtttgcctgg gccttggacg tcttggccaa cgcctccgt    960 cccatgcacg tctttatcct ggattacgac caatcgcccg ccggctgccg ggacgccctg   1020
ctgcaactta cctccgggat ggtccagacc cacgtcacca ccccaggctc cataccgacg   1080
atctgcgacc tggcgcgcac gtttgcccgg gagatggggg aggctaactg a           1131
```

<210> SEQ ID NO 14
<211> LENGTH: 658
<212> TYPE: PRT
<213> ORGANISM: Artificial Sequence
<220> FEATURE:
<223> OTHER INFORMATION: Protein sequence CAR CD44v6-NWL

<400> SEQUENCE: 14

```
Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Ile Asn Tyr Ile Tyr Trp Leu Gln Gln Lys Pro Gly Gln Ala Pro Arg
    50                  55                  60

Ile Leu Ile Tyr Leu Thr Ser Asn Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Leu Gln Trp Ser Ser
            100                 105                 110

Asn Pro Leu Thr Phe Gly Gly Gly Thr Lys Val Glu Ile Lys Arg Gly
        115                 120                 125

Gly Gly Gly Ser Gly Gly Gly Gly Ser Glu Val Gln Leu Val Glu Ser
    130                 135                 140

Gly Gly Gly Leu Val Lys Pro Gly Gly Ser Leu Arg Leu Ser Cys Ala
145                 150                 155                 160

Ala Ser Gly Phe Thr Phe Ser Ser Tyr Asp Met Ser Trp Val Arg Gln
                165                 170                 175

Ala Pro Gly Lys Gly Leu Glu Trp Val Ser Thr Ile Ser Ser Gly Gly
            180                 185                 190

Ser Tyr Thr Tyr Tyr Leu Asp Ser Ile Lys Gly Arg Phe Thr Ile Ser
        195                 200                 205

Arg Asp Asn Ala Lys Asn Ser Leu Tyr Leu Gln Met Asn Ser Leu Arg
    210                 215                 220
```

```
Ala Glu Asp Thr Ala Val Tyr Tyr Cys Ala Arg Gln Gly Leu Asp Tyr
225                 230                 235                 240

Trp Gly Arg Gly Thr Leu Val Thr Val Ser Ser Gly Asp Pro Lys Glu
            245                 250                 255

Ala Cys Pro Thr Gly Leu Tyr Thr His Ser Gly Glu Cys Cys Lys Ala
            260                 265                 270

Cys Asn Leu Gly Glu Gly Val Ala Gln Pro Cys Gly Ala Asn Gln Thr
            275                 280                 285

Val Cys Glu Pro Cys Leu Asp Ser Val Thr Phe Ser Asp Val Val Ser
            290                 295                 300

Ala Thr Glu Pro Cys Lys Pro Cys Thr Glu Cys Val Gly Leu Gln Ser
305                 310                 315                 320

Met Ser Ala Pro Cys Val Glu Ala Asp Asp Ala Val Cys Arg Cys Ala
                325                 330                 335

Tyr Gly Tyr Tyr Gln Asp Glu Thr Thr Gly Arg Cys Glu Ala Cys Arg
            340                 345                 350

Val Cys Glu Ala Gly Ser Gly Leu Val Phe Ser Cys Gln Asp Lys Gln
            355                 360                 365

Asn Thr Val Cys Glu Glu Cys Pro Asp Gly Thr Tyr Ser Asp Glu Ala
370                 375                 380

Asn His Val Asp Pro Cys Leu Pro Cys Thr Val Cys Glu Asp Thr Glu
385                 390                 395                 400

Arg Gln Leu Arg Glu Cys Thr Arg Trp Ala Asp Ala Glu Cys Glu Glu
                405                 410                 415

Ile Pro Gly Arg Trp Ile Thr Arg Ser Thr Pro Pro Glu Gly Ser Asp
            420                 425                 430

Ser Thr Ala Pro Ser Thr Gln Glu Pro Glu Ala Pro Pro Glu Gln Asp
            435                 440                 445

Leu Ile Ala Ser Thr Val Ala Gly Val Val Thr Thr Val Met Gly Ser
    450                 455                 460

Ser Gln Pro Val Val Thr Arg Gly Thr Thr Asp Asn Pro Lys Phe Trp
465                 470                 475                 480

Val Leu Val Val Val Gly Gly Val Leu Ala Cys Tyr Ser Leu Leu Val
                485                 490                 495

Thr Val Ala Phe Ile Ile Phe Trp Val Arg Ser Lys Arg Ser Arg Leu
            500                 505                 510

Leu His Ser Asp Tyr Met Asn Met Thr Pro Arg Arg Pro Gly Pro Thr
    515                 520                 525

Arg Lys His Tyr Gln Pro Tyr Ala Pro Pro Arg Asp Phe Ala Ala Tyr
    530                 535                 540

Arg Ser Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
            565                 570                 575

Glu Tyr Asp Val Leu Asp Lys Arg Gly Arg Asp Pro Glu Met Gly
            580                 585                 590

Gly Lys Pro Arg Arg Lys Asn Pro Gln Glu Gly Leu Tyr Asn Glu Leu
            595                 600                 605

Gln Lys Asp Lys Met Ala Glu Ala Tyr Ser Glu Ile Gly Met Lys Gly
    610                 615                 620

Glu Arg Arg Arg Gly Lys Gly His Asp Gly Leu Tyr Gln Gly Leu Ser
625                 630                 635                 640
```

```
Thr Ala Thr Lys Asp Thr Tyr Asp Ala Leu His Met Gln Ala Leu Pro
            645                 650                 655
Pro Arg
```

CAR NK CELLS

CROSS-REFERENCE TO RELATED APPLICATION

This application is the U.S. national phase of PCT Application No. PCT/EP2019/063920 filed on May 29, 2019, which claims priority to EP Patent Application No. 18175055.5 filed on May 30, 2018, the disclosures of which are incorporated in their entirety by reference herein.

SEQUENCE LISTING

The text file eolf-seql of size 19 KB created Dec. 5, 2019, filed herewith, is hereby incorporated by reference.

FIELD OF THE INVENTION

The present invention relates to the field of manufacturing of Natural Killer (NK) Cells genetically modified with lentiviral vectors carrying a polynucleotide coding for a Chimeric Antigen Receptors (CARs). The present invention further relates to CAR-NK cells and use of the CAR-NK cells in medicine, in particular for treating cancer.

BACKGROUND TO THE INVENTION

The present invention is focused on the development of a manufacturing process of Natural Killer Cells genetically modified with a lentiviral vector carrying at least one polynucleotide coding for a CAR (CAR-NK cells). The manufacturing method of the invention allows obtaining a cellular population characterized by effective synergy between the therapeutic effect of the NK cells and of the CAR.

Natural Killer Cells (NK cells), are cells of the innate immune system with high antitumour, antiviral and antimicrobial activity. The use of NK cells for the treatment of cancer has attracted interest after successful adoptive transfers and in vivo expansions of NK cells had been reported in patients with cancer [Ruggeri et al (2005) Curr Opin Immunol 17: 211-7; Ren et al (2007) Cancer Biother Radiopharm 22: 223-34; Koehl et al (2004) Blood Cells Mol Dis 33: 261-6.176 Passweg et al (2004) Leukaemia 18:1835-8]. In general, donor NK cell infusions were well tolerated without evidence for induction of GvHD in these studies. However, only a few trials investigating adoptive NK cell infusions in patients with cancer have been conducted to date. A major obstacle is that only relative small numbers of NK cells can be isolated from regular leukapheresis products. This hampers clinical trials for NK-cell dose dependent anti-tumour responses in humans with cancer [Klingemann et al (2004) Cytotherapy 6: 15-22; Passweg et al (2006) Best Pract Res Clin Haematol 19: 811-824; McKenna et al (2007) Transfusion 47: 520-528; Koehl et al (2005) Klin Padiatr 217: 345-350; Iyengar et al (2003) Cytotherapy 5: 479-484; Meyer-Monard et al (2009) Transfusion 49: 362-371]. Therefore, ex vivo protocols for expansion and activation of NK cells are under investigation enabling clinical trials at higher NK cell dosages and to permit multiple NK cell infusions[Carlens et al (2001) Hum Immunol 62: 1092-1098; Barkholt et al (2009) Immunotherapy 1: 753-764; Berg et al (2009) Cytotherapy 11: 341-355; Fujisaki et al (2009) Cancer Res 69: 4010-4017; Siegler et al. (2010) Cytotherapy 12(6):750-63]. However, most protocols deal with technical disadvantages by using supportive feeder cell lines that could lead to regulatory problems producing NK cell products for large-scale and multi-center trials. Previously, we have described an alternative cytokine-based culture method with the capability of generating clinically relevant NK cell products with high cell numbers, high purity and functionality from CD34+ hematopoietic stem cells [Spanholtz et al (2010) PLoS One 5: e9221]. We have further optimized the enrichment of CD34+ and developed a scalable procedure that results in high yields of activated CD34+ cells-derived NK cells. Chimeric Antigen Receptors (CARs) are recombinant receptors that recognize a specific protein or antigen expressed on a target cell. Once expressed in T lymphocytes, which is then called a CAR-T cell, or other cells of the immune system, CARs are able to redirect a specific immune response against all cells that express the antigen they bind to. The most largely explored clinical application of CARs is the cancer immunotherapy, which consists in the infusion of cells of the immune system, such as T cells or NK cells, carrying a CAR targeted to a tumour antigen. Such cells are able to generate a strong antitumour response against cells expressing the antigen targeted by the CAR (Sadelain et al., Cancer Discovery. 2013. 3(4):388-98).

CARs are recombinant chimeric proteins that consist of an ectodomain responsible of antigen recognition, commonly derived from a single chain variable fragment (scFv), a spacer region, a transmembrane domain, and an endodomain that transmits activation and costimulatory signals to the cells in which they are expressed. Depending on the number of signaling domains, CARs are classified into 1st generation (one), 2nd generation (two), or 3rd generation (three) CARs (Dotti et al., Immunol Rev. 2014 January; 257(1)).

The "spacer" or "hinge" region, is the connecting sequence between the ectodomain and the transmembrane domain. The most common sequence used as spacer is the constant immunoglobulin IgG1 hinge-CH2-CH3 Fc domain. WO 2016/042461 discloses CARs comprising spacer regions deriving from the extracellular domain of the human low affinity nerve growth factor receptor (LNGFR).

Several CAR-T cell candidates are now in clinical development and different successful cases are emerging. The Food and Drug Administration (FDA) recently approved tisagenlecleucel (Kymriah®), the first CAR T-cell therapy indicated for the treatment of patients up to 25 years of age affected by B-cell precursor acute lymphoblastic leukaemia (ALL) that is refractory or in second or later relapse, and axicabtagene ciloleucel (Yescarta®), indicated for the treatment of adult patients with relapsed or refractory large B-cell lymphoma after two or more lines of systemic therapy.

The majority of CAR-T cells studies have used autologous T cells, because allogeneic T-cells carry a significant risk to develop Graft versus Host Disease (GvHD), a serious and potentially lethal adverse event which consists in an aggression against the host tissues by the allogeneic T-cells. The manufacturing of autologous CAR-modified T cells is patient specific and has some practical limitations.

The development of NK-cells genetically modified to express a CAR (CAR-NK cells) is still in earlier stage of development. Preclinical and clinical studies performed using CAR-NK cells targeting different antitumour agents are reviewed in Martin-Antonio et al. Int J Mol Sci. 2017 Aug. 29; 18(9).

CAR-NK cells are expected to have several advantages compared to CAR-T cells. In respect to the manufacturing, since NK-cells do not cause GvHD, they offer the opportunity to produce an off-the-shelf allogeneic product available for immediate clinical use. In addition, autologous and allogeneic NK cells have a limited in vivo persistence which makes the occurring of life threatening toxicities like cytokines release syndrome less likely. From an efficacy perspective, once engineered with CARs, NK cells should retain their native receptors thus allowing antitumour effect mediated by mechanisms others than those mediated by CAR specificity (Rezvani et al. Mol. Ther. Aug. 2017; 25 (8)).

Different strategies for NK-cells engineering are currently under development. The majority of preclinical and early clinical studies published so far on CAR-NK cells have utilized NK cell lines to express CAR molecules (Martin-Antonio et al. Int J Mol Sci. 2017 Aug. 29; 18(9) with the NK-92 cell line the most widely studied. Despite some potential advantages for the manufacturing, NK-92 cells have significant clinical drawbacks to be taken into consideration: potential tumourigenicity since they derive from a patient affected by Non-Hodgkin Lymphoma, multiple cytogenetic abnormalities, and latent infection with Epstein-Barr virus (EBV). For these reasons NK-92 are irradiated prior to clinical use. Such irradiation may have negative impact on in vivo proliferation and persistence and definitively on antitumour activity of CAR-NK cells. Some authors disclosed CAR-NK cells obtained starting from primary human NK cells derived from peripheral blood or umbilical cord blood, genetically modified by viral transduction or other alternative non-viral transduction methods. Great variability was observed with these approaches due to different NK function among different donors, as well as the impact of transduction methods and expansion strategies (Rezvani et al. Mol. Ther. Aug. 2017; 25 (8)).

The present invention is focused on the development of a manufacturing process of CAR-NK cells starting from stem cells purified from biological samples, which are genetically modified to express the CAR and then differentiated into CAR-NK. The inventors found the conditions to perform each step of the manufacturing process in order to obtain a cellular population containing CAR-NK cells in which NK-cells antitumour activity and CAR antitumour activity act synergistically.

Prior art discloses some protocols which follow similar approaches but in no case prior publications describe the impact of the transduction conditions on the nature and composition of intermediate CAR-CD34+ stem cellular population as well as on the therapeutic effect of the final CAR-NK cellular population.

For example, Lowe et al. Met. Mol. Biol. 2016; 1441: 241-2511 disclose two protocols for production of CAR-NK cells starting from cord blood derived human hematopoietic stem cells (HSC) that are modified to express chimeric antigen receptors. In both protocols LVV transduction is performed in a medium supplemented with Flt3, SCF and TPO in the presence of RetroNectin®. Transduced stem cells are then differentiation into NK-cells using co-culture with a feeder stroma of murine OP9-DL1 cells (protocol 1) or using a feeder-free protocol based on culturing cells in AIM V medium supplemented with SCF, recombinant human Flt-3 ligand, IL-15 and IGF-1 (protocol 2). The paper does not disclose of the manufacturing method of the present invention and the impact of the conditions used on the antitumour effect of the final population of CAR-NK cells.

Ni et al. Stem Cells. 2014 April; 32(4) disclose a further protocol for production of CAR-NK cells to be used for the treatment of HIV infection. In this case, human embryonic stem cells or induced pluripotent stem cells are transduced with LVV carrying a CAR then cultured for 11 days in BPEL media with stem cell factor, vascular endothelial growth factor and bone morphogenic protein 4 and then differentiated into NK cells in the presence of EL08-1D2 stromal cells. The paper does not disclose the conditions of the method of the present invention and, interestingly, and it clearly shows that while in vitro CAR-NK cells are able to inhibit HIV replication in CD4+ T cells more efficiently than their unmodified counterparts, in vivo there is no significant increase of efficacy of CAR modified NK cells versus unmodified NK cells. Therefore, in this approach, there is no in vivo observation of synergy between NK cells and the CAR.

There is a need to develop a manufacturing method that allows obtaining CAR-NK cells in sufficient quantity and quality to be used in medical treatments, characterized by a synergistic effect between NK-cells and CAR therapeutic effects. The present invention addresses this need.

SUMMARY OF THE INVENTION

The present invention relates to the development of a manufacturing process of CAR-NK cells that allows obtaining a cellular population characterized by effective synergy between the therapeutic effect of NK cells and Chimeric Antigen Receptors (CARs).

The manufacturing process includes a first phase aimed to produce, using lentiviral vector transduction, an intermediate cellular population containing CD34+ stem cells genetically modified to express at least one polynucleotide coding for a CAR, and a second phase in which the intermediate cellular population is expanded and differentiated into a cellular population containing CAR-NK cells. Prior art discloses some methods to obtain CAR-NK cells based on the idea of viral transduction of CD34+ stem cells from biological sources, followed by differentiation into CAR-NK cells. None of such methods discloses the conditions of the method of the present invention. Moreover, by comparing different protocols, the inventors surprisingly found that the different transduction and culturing conditions had an effect on the nature and the composition of the intermediate population of cells and, consequently, on the final differentiated CAR-NK cellular population which results in a different therapeutic effect. CAR-NK cellular population obtainable by the manufacturing method of the invention has a stronger therapeutic effect in vivo.

The method of the invention comprises two phases:

In the first phase CD34+ stem cells are purified from a biological sample and genetically engineered by transduction with lentiviral vectors carrying a polynucleotide coding for a CAR. Lentiviral transduction is performed in the presence of a culture medium comprising a collection of cytokines, thus obtaining an intermediate cellular population containing CAR-CD34+ stem cells, which, optionally, are further expanded in the culture medium comprising the collection of cytokines.

In the second phase the intermediate cellular population is (further) expanded and differentiated into a cellular population containing CAR-NK cells. The CAR-CD34+ stem cells obtained from phase I are preferably cultured in a second and in a third medium having a collection of cytokines, different from said first culture medium, thereby obtaining a collection of cultured cells containing a plurality of CAR-NK cells or CAR-NK progenitor cells or both.

It was surprisingly found that the conditions applied for the performance of the method of the present invention allows obtaining a CAR-NK population having a stronger therapeutic effect resulting from the synergy between intrinsic antitumour effect of the NK-cells and the CAR.

DESCRIPTION OF THE DRAWINGS

FIG. 4. A. In vitro functionality data (%7AAD+) from MOCK NK (non T) and CD44v6 CAR-NK (T) cells for condition A and B against K562, T98G and THP-1 tumour cell lines, respectively sensitive-, intermediate- or resistant to NK-cell cytotoxicity. B. In vitro functionality data (%7AAD+) from MOCK NK (non T) and CD44v6 CAR-NK (T) cells for condition A and B against a sensitive tumour cell line (K562) after reconstitution. C. Degranulation (% CD107a+) of MOCK NK (non T) and CD44v6 CAR-NK (T) cells for condition A and B against a sensitive tumour cell line (K562) after reconstitution.

FIG. 5. A Inhibiting and activating receptor expression of MOCK NK (non T) and CD44v6 CAR-NK (T) cells from condition A before reconstitution. B. Inhibiting and activating receptor expression of MOCK NK (non T) and CD44v6 CAR-NK (T) cells for condition A and B after reconstitution.

DETAILED DESCRIPTION OF THE INVENTION

Figure 1:
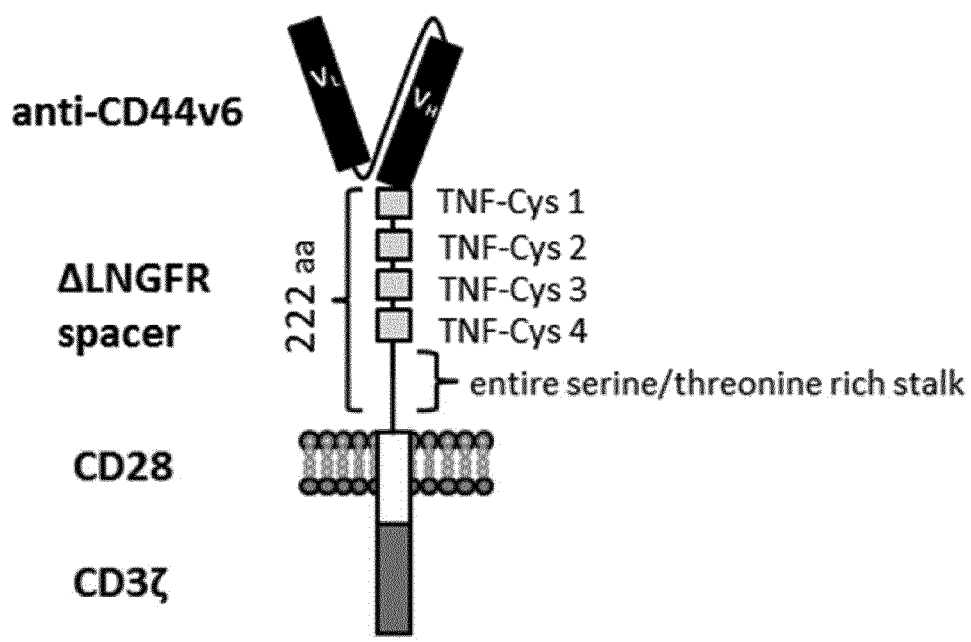
FIG. 1. The figure shows the schematic structure of the CAR CD44v6 wild-type long (CD44v6-NWL) containing a CD44v6 binding domain, the LNGFR wild-type long spacer (including the four TNFR-Cys domains and the entire serine threonine rich stalk) the transmembrane and co-stimulatory domain of CD28 and the intracellular domain of CD3 ☐☐chain.

Various preferred features and embodiments of the present invention will now be described by way of non-limiting exemplifying embodiments.

The present invention provides a method for the manufacturing of a population of NK-cells genetically modified with a Chimeric Antigen Receptor (CAR). The method of the invention allows obtaining a cellular population in which therapeutic effects of NK-cells and CAR act synergistically. The inventors found the optimal conditions to obtain such synergy. The process includes two phases: the first one aimed to the production of an intermediate cellular population containing stem cells genetically modified to express the CAR i.e. the intermediate population containing CAR-CD34+ stem cells, and the second phase in which such intermediate cellular population is expanded and differentiated into a cellular population containing CAR-NK cells.

In one embodiment there is provided a method for the manufacturing of a population of NK-cells, genetically modified with a Chimeric Antigen Receptor (CAR) comprising:

(i) A first phase of production of an intermediate cellular population containing CD34+ cells carrying at least one polynucleotide coding for a CAR according to the following steps:
  a) obtaining a biological starting sample selected from the group consisting of bone marrow, peripheral blood, placenta or umbilical cord blood,
  b) isolating hematopoietic stem cells from such biological sample,
  c) culturing the isolated hematopoietic stem cells in the presence of a culture medium I,
  d) transducing cultured stem cells by incubating such cells with a lentiviral vector carrying at least a polynucleotide coding for a CAR, thus obtaining an intermediate cellular population containing CAR-CD34+ stem cells, and
  e) optionally, culturing the intermediate cellular population containing CAR-CD34+ stem cells in culture medium I for at least one day, wherein culture medium I is a basic culture medium, comprising a collection of cytokines, wherein said collection of cytokines comprises Interleukin-7 and one or more of stem cell factor (SCF), flt-3Ligand (FLT-3L), thrombopoietin (TPO), and two or more of granulocyte-macrophage-colony-stimulating factor (GM-CSF), granulocyte-colony-stimulating factor (G-CSF), and interleukin-6 (IL-6), (ii) a second phase comprising:
  an optional, preliminary step of further expanding the intermediate cellular population containing CAR-CD34+ stem cells from the first phase in culture medium II, thereby obtaining a cellular population containing CAR-CD34+ stem cells and CAR-NK progenitor cells, wherein culture medium II is a basic culture medium comprising a collection of cytokines, wherein said collection of cytokines comprises two or more of SCF, FLT-3L interleukin-15 (IL-15) and IL-7 and two or more of GM-CSF, G-CSF, and IL6, and
  a step of expanding and differentiating the intermediate cellular population collected from phase I containing CAR-CD34+ stem cells or the cellular population collected from the optional preliminary step containing CAR-CD34+ stem cells and CAR-NK progenitor cells into a cellular population containing CAR-NK cells, the step comprising culturing the intermediate cellular population from phase I containing CAR-CD34+ stem cells or the cellular population from the optional preliminary step containing CAR-CD34+ stem cells and CAR-NK progenitor cells in culture medium III, thereby obtaining a cellular population containing NK-cells wherein the culture medium III is a basic culture medium comprising a collection of cytokines, wherein said collection of cytokines comprises two or more of SCF, IL-7, IL-15 and interleukin-2 (IL-2) and two or more of GM-CSF, G-CSF, and IL-6.

For culturing and transducing a total of three different media is used:

Culture medium I is a basic culture medium, comprising a collection of cytokines, wherein said collection of cytokines comprises interleukin-7 (IL-7) and one or more of stem cell factor (SCF), flt-3Ligand (FLT-3L), thrombopoietin (TPO), and two or more of granulocyte-macrophage-colony-stimulating factor (GM-CSF), granulocyte-colony-stimulating factor (G-CSF), and interleukin-6 (IL-6). Preferably the collection of cytokines comprises IL-7 and two or more of SCF, FLT-3L, and TPO, more preferably the collection of cytokines comprises SCF, FLT-3L, TPO and IL-7. In a preferred embodiment the collection of cytokines comprises GM-CSF, G-CSF, and IL-6. It is particularly preferred that the culture medium I comprises SCF, FLT-3L, TPO, IL-7, GM-CSF, G-CSF, and IL-6.

Culture medium II is a basic culture medium comprising a collection of cytokines, wherein said collection of cytokines comprises two or more of SCF, FLT-3L interleukin-15 (IL-15) and IL-7 and two or more of GM-CSF, G-CSF, and IL-6. Preferably the collection of cytokines comprises three or more of SCF, FLT-3L, IL-15, and IL-7, more preferably the collection of cytokines comprises SCF, FLT-3L, IL-15 and IL-7. In a preferred embodiment the collection of cytokines comprises GM-CSF, G-CSF, and IL-6. It is particularly preferred that the culture medium II comprises SCF, FLT-3L, IL-15, IL-7, GM-CSF, G-CSF, and IL-6.

Culture medium III is a basic culture medium comprising a collection of cytokines, wherein said collection of cytokines comprises two or more of SCF, IL-7, IL-15 and interleukin-2 (IL-2) and two or more of GM-CSF, G-CSF, and IL-6. Preferably the collection of cytokines comprises three or more of SCF, IL-7, IL-15, and IL-2, more preferably the collection of cytokines comprises SCF, IL-7, IL-15 and IL-2. In a preferred embodiment the collection of cytokines comprises GM-CSF, G-CSF, and IL-6. It is particularly preferred that the culture medium III comprises SCF, IL-7, IL-15, IL-2, GM-CSF, G-CSF, and IL-6.

First Phase: Production of the Intermediate Population Containing CAR-CD34+ Stem Cells (i) The first phase of the method of the invention provides the conditions to produce an intermediate cellular population containing CD34+ stem cells carrying at least one polynucleotide coding for a CAR. The intermediate cellular population is produced according to the following steps:
   a) obtaining a biological starting sample selected from the group consisting of bone marrow, peripheral blood, placenta or umbilical cord blood,
   b) isolating hematopoietic stem cells from such biological sample,
   c) culturing the isolated hematopoietic stem cells in the presence of a culture medium I,
   d) transducing cultured stem cells by incubating such cells with a lentiviral vector carrying at least a polynucleotide coding for a CAR, thus obtaining an intermediate cellular population containing CAR-CD34+ stem cells, and
   e) optionally, culturing the intermediate cellular population containing CAR-CD34+ stem cells in culture medium I for at least one day, wherein culture medium I is a basic culture medium, comprising a collection of cytokines, wherein said collection of cytokines comprises Interleukin-7 and one or more of stem cell factor (SCF), flt-3Ligand (FLT-3L), thrombopoietin (TPO), and two or more of granulocyte-macrophage-colony-stimulating factor (GM-CSF), granulocyte-colony-stimulating factor (G-CSF), and interleukin-6 (IL-6).

The starting material to be used in the method of the present invention is a biological sample containing adult (postembryonic) stem cells also called somatic stem cells. As used herein the term biological sample means a sample derived from human being. In a preferred embodiment the starting material to be used is the umbilical cord blood.

According to the method of the invention CD34+ stem cells are isolated from the biological sample. Different protocols are known in the art for CD34+ isolation including methods based on immunomagnetic selection or cell sorting. As used herein, immunomagnetic selection refers to the coupling of antibodies to magnetic particles thus enabling separation of the antigenic structures by the use of a magnet.

In a preferred embodiment the biological sample is first enriched for mononuclear cells using gradient separation or centrifugation techniques and then is subject to immunomagnetic selection by labelling cells with specific anti-CD34+ antibody conjugated to magnetic beads and purifying CD34+ cells using magnetic columns. In a further preferred embodiment immunomagnetic separation is performed using MidiMACS™ Separator, CliniMACS® Plus Instrument or CliniMACS Prodigy® devices.

During the first phase of the method of the invention isolated CD34+ stem cells are first cultured and then transduced in the presence of a basic medium comprising a cocktail of cytokines and growth factors. Many basic culture media are known. A selection is given below, but many more may be suitable. Basic media include but are not limited to BEM (Basic Eagle Medium), DMEM (Dulbecco's modified Eagle Medium), Glasgow minimal essential medium, M199 basal medium, HAMs F-10, HAMs F-12, Iscove's DMEM, RPMI, Leibovitz L15, MCDB, McCoy 5A, StemSpan H3000® and StemSpanSFEM®, Stemline I™ and Stemline II™, Glycostem Basal growth medium (GBGM™); X-Vivo10™, X-Vivo15™ and X-Vivo20™ CellGenix® Stem Cell Growth Medium, etc. Combinations of these basic media can also be used. Preferably serum-free formulations, such as Stemline I™ and Stemline II™, StemSpan H3000@, StemSpan SFEM® or X-Vivo10™, GBGM™ X-Vivo15™ and X-Vivo20™ are used at the time point of initiation of culture with and/or without the addition of human serum. Alternatively, or in addition, basic culture medium may be complemented with other (human) blood derivative, such as platelet lysate, autologous or allogeneic donor serum, (platelet rich) plasma, albumin, or a synthetic alternative to serum, such as, e.g., globulin enriched protein supplement. The amounts given herein are typically suitable for cultures. The amounts may be adapted for different amounts of cells with which cultures are started. The media used in the various culturing steps according to the invention can be varied in their serum content, preferably together with a different combination of cytokines to provide either an expansion medium or a differentiation medium and or alternatively an expansion+ differentiation medium at defined time points according to the invention.

Upon isolation, CD34+ stem cells are seeded in containers such as plates, flasks, cell factories or bags at concentration ranging from $0.5 \times 10^6$ to $2 \times 10^6$ cells/ml. In a preferred embodiment cells are seeded at concentration $1 \times 10^6$ cells/ml.

In one embodiment the cells are seeded in containers previously coated with fragments of fibronectin, for example the fragment CH-296 (RetroNectin®) or functional derivatives. When coated on the surface of cell containers RetroNectin® significantly enhances viral vector mediated gene transduction into mammalian cells. In a preferred embodiment, cell containers are coated with RetroNectin®.

Once seeded, the stem cells are cultured in a culture medium I. In one embodiment culturing phase may be performed for a period of at least 12-48 hours, more preferably 22+/−2 hours. In one preferred embodiment the culture medium I comprises one or more 30 of the cytokines at the following ranges of concentration: GM-CSF between 2-100 pg/ml, preferably between 5-50 pg/ml, most preferably about 10 pg/ml, G-CSF between 100 and 1000 pg/ml, preferably between 150 and 500 pg/ml, most preferably about 250 pg/ml, SCF between 4 ng/ml and 300 ng/ml, preferably between 10 and 100 ng/ml, most preferably about 25 ng/ml, Flt3-L between 4 ng/ml and 300 ng/ml, preferably between 10 and 100 ng/ml, most preferably about 25 ng/ml, TPO between 4 ng/ml and 100 ng/ml, preferably between 10 and 50 ng/ml, most preferably about 25 ng/ml, IL-6 between 5-500 pg/ml, preferably between 25-100 pg/ml, most preferably, about 50 pg/ml, and/or IL7 between 4 ng/ml and 100 ng/ml, preferably between 10 and 50 ng/ml, most preferably about 25 ng/ml. In a more preferred aspect of the invention, the culture medium I includes cytokines at a concentration of about 25 ng/ml. SCF, about 25 ng/ml Flt3-L, about 25 ng/ml TPO, about 250 pg/ml G-CSF, about 10 pg/ml GM-CSF, about 50 pg/ml IL-6, and about 25 ng/ml IL7. With "about" is meant in this context a deviation of about 20%, preferably 10%, more preferably 5%, most preferably 2%.

In one particular preferred embodiment, a method according to the invention is provided, wherein culture medium I includes SCF at concentration between 4 ng/ml and 300 ng/ml, or Flt3-L at concentration between 4 ng/ml and 300 ng/ml, or TPO at concentration between 4 ng/ml and 100 ng/ml, or IL7 at concentration between 4 ng/ml and 50 ng/ml, or any combination of these cytokines in the specified ranges of concentrations.

In a more preferred embodiment, a method according to the invention is provided, wherein culture medium I includes GM-CSF at concentration between 2 pg/ml and 100 pg/ml, or G-CSF at concentration between 100 pg/ml and 1000 pg/ml, or IL6 between 5-500 pg/ml, or any combination of these cytokines in the specified ranges of concentrations.

Preferably, culture medium I comprises between 4-100 μg/ml heparin, preferably between 10-40 μg/ml heparin, more preferably about 20 μg/ml heparin. Preferably, culture medium I comprises between 0.5-25% serum, more preferably between 1-20% serum, most preferably about 10% serum. Preferably, the serum is human serum. In another preferred embodiment, the culture media I, II and III, independently from one another, comprise another (human) blood derivative, such as platelet lysate, autologous or allogeneic donor serum, (platelet rich) plasma, albumin, or a synthetic alternative to serum, such as, e.g., globulin enriched protein supplement. The optimal concentrations of such alternatives to serum can easily be determined by the skilled person.

After the step of culturing, the CD34+ stem cells are genetically modified to express at least one polynucleotide coding for a CAR. The technology used to perform genetic engineering of stem cells is the lentiviral transduction. As used herein the terms transduction or lentiviral transduction refer to the introduction of foreign polynucleotide into a cell's genome using lentiviral vectors. The term lentiviral vector is used to refer to a lentiviral particle that mediates nucleic acid transfer.

According to a method of the invention transduction is performed by incubating CD34+ stem cells with lentiviral vectors carrying at least one polynucleotide coding for a CAR, in the presence of a culture medium I. In one embodiment, the incubation is performed by substituting at least half of the culture medium with fresh culture medium I, containing lentiviral vectors carrying a polynucleotide coding for a CAR.

In another embodiment the incubation is performed by re-suspending the CD34+ stem cells in fresh culture medium I containing lentiviral vectors carrying a polynucleotide coding for a CAR, such resuspension is then seeded in a cell container at a concentration ranging from $1 \times 10^6$ to $10 \times 10^6$ cell/ml, preferably from $2 \times 10^6$ to $5 \times 10^6$ cell/ml, most preferably about $2 \times 10^6$.

As used herein the terms "run of transduction" refers to a single cycle of incubation of CD34+ stem cells with fresh lentiviral vector. The period of time for incubation may vary depending on the nature of the lentiviral vector. In a preferred embodiment during a run of transduction CD34+ stem cells may be incubated with lentiviral vectors for period of time from 10 to 24 hours, preferably from 13 to 20 hours more preferably about 15 hours. With "about" is meant in this context a deviation of about 20%, preferably 10%, more preferably 5%, most preferably 2%. According to the method of the invention the transduction may include one or more transduction runs. In another aspect of the invention the cell container may be coated with RetroNectin®.

Transduction may be performed in the presence of further additives that enhances efficiency of transduction such as polybrene, protamine sulphate or chondroitin sulphate. Lentiviral vectors may be incubated with CD34+ stem cells at different concentration depending on the nature of the vector. Preferably transduction is performed by incubation of lentiviral vectors at Multiplicity of Infection (MOI) ranging from 10 to 200. The MOI is the ratio of the number of lentiviral vector particles to the number of target cells present in a defined space. In a preferred embodiment lentiviral vectors are incubated at about MOI 100.

The transduction results in the production of the intermediate cellular population containing CAR-CD34+ stem cells carrying at least one polynucleotide encoding a CAR.

The so obtained intermediate cellular population containing CAR-CD34+ stem cells may be cultured for at least one further day in the presence of fresh culture medium I before moving to the second phase of the manufacturing method.

In another embodiment the intermediate cellular population containing CAR-CD34+ stem cells may be frozen at the end of the transduction. In another embodiment the intermediate cellular population may be cultured for at least one further day in the presence of fresh culture medium I and then may be frozen.

The second phase of the manufacturing can be performed after the end of the transduction or after one or more days of culture, or upon thawing of frozen intermediate cellular population containing CAR-CD34+ stem cells. Preferably, the second phase is performed after a total of at least 7 culturing days in culture medium I.

In one embodiment of the invention there is provided an intermediate cellular population containing CAR-CD34+ stem cells obtainable by the first phase of the method of the present invention.

In another embodiment, the first phase of the method of the invention may further include a step of selection of CAR-CD34+ stem cells thus obtaining a pure population of CAR-CD34+ stem cells. The skilled man may apply different methods known in the art to select CAR-CD34+ stem cells. In one embodiment CD34+ stem cells may be transduced with a lentiviral vector carrying one polynucleotide coding for a CAR and a further polynucleotide coding for a selectable protein not normally expressed by the CD34+ cells to be used as a marker for immune-selection.

Examples of selectable proteins suitable for being used as markers are truncated forms of receptors proteins such as for example the extracellular domains of the human low affinity nerve growth factor (□LNGFR), the human epidermal growth factor receptor, the CD19 or the CD20. In this way, transduced CAR-CD34+ stem cells will co-express the CAR and the selectable protein and, therefore, they may be selected using immunomagnetic selection methods by labelling cells with specific antibodies targeted to the selectable marker, such antibodies being conjugated to magnetic beads, and purifying CAR-CD34+ cells using magnetic columns. In a further preferred embodiment immunomagnetic separation is performed using MidiMACS™ Separator, CliniMACS® Plus Instrument or CliniMACS Prodigy® devices.

In another preferred embodiment CAR-CD34+ stem cells may be selected by immunomagnetic selection methods in which the antibodies are targeted to selectable regions of the CAR molecule. For example, CD34+ stem cells may be transduced with a lentiviral vector carrying one polynucleotide coding for a CAR, such CAR containing a spacer domain for use as a marker for immune-selection i.e. a spacer domain that can be specifically recognized by an antibody conjugated to magnetic beads, thus allowing purification of CAR-CD34+ cells using magnetic columns. Preferably immunomagnetic separation is performed using MidiMACS™ Separator, CliniMACS® Plus Instrument or CliniMACS Prodigy® devices. Preferably the spacer domain for use as marker is derived from the extracellular domain of proteins not normally expressed by the CD34+ cells. In a further preferred embodiment CD34+ stem cells may be transduced with a lentiviral vector carrying one polynucleotide coding for a CAR, wherein the CAR contain a spacer domain derived by the extracellular domain of one of human low affinity nerve growth factor ($\Delta$LNGFR).

As said before, the culture conditions wherein the transduction takes place (i.e. culturing in culture medium I) are preferably continued for a total of at least 7 days, i.e. including culturing before transduction, culturing during transduction runs 1 and 2, and culturing after transduction. Thereafter, a second phase, comprising expansion and differentiation into NK cells is initiated.

Second Phase: Expansion and Differentiation of the Intermediate Cellular Population Containing CAR-CD34+ Stem Cells into a Cellular Population Containing CAR-NK Cells The second phase of the method of the invention provides the conditions in which the intermediate cellular population (or a further expanded cellular population (see below) is expanded and differentiated into a cellular population containing CAR-NK cells comprising culturing the intermediate (or further expanded) cellular population containing CAR-CD34+ stem cells from the first phase in culture medium III, thereby obtaining a cellular population containing NK-cells, wherein the culture medium III is a basic culture medium comprising a collection of cytokines, wherein said collection of cytokines comprises two or more of SCF, IL-7, IL-15 and interleukin-2 (IL-2) and two or more of GM-CSF, G-CSF, and IL-6. The intermediate cellular population (or further expanded cellular population) is cultured for at least 7 days in culture medium III, thereby obtaining a collection of cultured cells containing a plurality of CAR-NK cells or CAR-NK progenitor cells or both.

In a further aspect of the invention the method, in the second phase, further comprises, a preliminary step of culturing of the intermediate cellular population containing CAR-CD34+ stem cells from the first phase in culture medium II thereby obtaining a cellular population containing CAR-CD34+ stem cells and CAR-NK progenitor cells wherein culture medium II is a basic culture medium comprising a collection of cytokines, wherein said collection of cytokines comprises two or more of SCF, FLT-3L interleukin-15 (IL-15) and IL-7 and two or more of GM-CSF, G-CSF, and IL6.

The preliminary culturing step with medium II is optional and is directed to obtaining more CAR-CD34+ stem cells or CAR-NK progenitor cells to enter culturing step with medium III which aims at differentiation. In this preliminary culturing step, the intermediate cellular population containing CAR-CD34+ stem cells collected from phase I are cultured for at least 4 days in culture medium II thereby obtaining a collection of cultured CAR-CD34+ stem cells, CAR-NK progenitor cells or both, containing a plurality of CAR-NK progenitor cells committed to the NK cell lineage.

In one preferred embodiment the culture medium II comprises one or more of the cytokines at the following ranges of concentration: G-CSF between 50 pg/ml and 1000 ng/ml, preferably between 150 and 400 ng/ml, GM-CSF between 2-100 pg/ml, preferably between 5-25 ng/ml, SCF between 4-300 ng/ml, preferably between 10-100 ng/ml, Flt3-L between 4 ng/ml and 300 ng/ml, preferably between 10 ng/ml and 100 ng/ml, I15 between 4 ng/ml and 300 ng/ml, preferably between 10 ng/ml and 100 ng/ml, IL-6 between 2 pg/ml and 500 pg/ml, preferably between 20 pg/ml and 200 pg/ml and/or IL7 between 4 ng/ml and 100 ng/ml, preferably between 10 ng/ml and 50 ng/ml. In a more preferred aspect of the invention, the culture medium II includes cytokines at a concentration of about 10 pg/ml GM-CSF, about 250 pg/ml G-CSF, about 25 ng/ml. SCF, about 25 ng/ml Flt3-L, about 20 ng/ml IL-15, about 50 pg/ml IL-6, and about 25 ng/ml IL7. With "about" is meant in this context a deviation of about 20%, preferably 10%, more preferably 5%, most preferably 2%. Preferably, culture medium II comprises between 4-100 pg/ml heparin, preferably between 10-40 pg/ml heparin, more preferably about 20 pg/ml heparin. Preferably, culture medium II comprises between 0.5.-25% serum, more preferably between 1-20% serum, most preferably about 10% serum. Preferably, the serum is human serum.

In one preferred embodiment the culture medium III comprises one or more of the cytokines at the following ranges of concentration: G-CSF between 50 pg/ml and 1000 ng/ml, preferably between 150 and 400 ng/ml, GM-CSF between 2 pg/ml and 100 pg/ml, preferably between 5 ng/ml and 25 ng/ml, SCF between 4 ng/ml and 300 ng/ml, preferably between 10 ng/ml and 100 ng/ml, IL-2 between 200 U/ml and 5000 U/ml, preferably between 500 and 2000 U/ml, IL15 between 4 ng/ml and 300 ng/ml, preferably between 10 ng/ml and 100 ng/ml, IL-6 between 2 pg/ml and 500 pg/ml, preferably between 20 pg/ml and 200 pg/ml and/or IL7 between 4 ng/ml and 100 ng/ml, preferably between 10 ng/ml and 50 ng/ml. In a more preferred aspect of the invention, the culture medium III includes cytokines at a concentration of about 10 pg/ml GM-CSF, about 250 pg/ml G-CSF, about 20 ng/ml. SCF, about 25 ng/ml, about 20 ng/ml IL-15, about 50 pg/ml IL-6, about 1000 U/ml IL-2, and about 20 ng/ml IL7. With "about" is meant in this context a deviation of about 20%, preferably 10%, more preferably 5%, most preferably 2%. Preferably, culture medium III comprises between 0.5-10% serum, more preferably between 1-5% serum, most preferably about 2% serum. Preferably, the serum is human serum.

Chimeric Antigen Receptors

Lentiviral vectors to be used in the method of the invention carry at least one polynucleotide coding for a CAR. The CARs to be used in the method of the present invention are recombinant chimeric receptors comprising:

(i) an antigen-specific targeting domain;
(ii) a spacer domain;
(iii) a transmembrane domain;
(iv) optionally at least one costimulatory domain; and
(v) an intracellular signalling domain.

The extracellular domain of the CAR to be used in the method of the present invention comprises an antigen-specific targeting domain that has the function of binding to the target antigen of interest.

The antigen-specific targeting domain may be any naturally occurring, synthetic, semi-synthetic, or a molecule produced recombinant technology, protein, peptide or oligo peptide that specifically binds to the target antigen.

Examples of possible antigen-specific targeting domains include antibodies or antibody fragments or derivatives, synthetic or naturally occurring ligands of the targeted receptor including molecules, binding or extracellular domains of receptors or binding proteins.

In a preferred embodiment, the antigen-specific targeting domain is, or is derived from, an antibody. An antibody is a protein, or a polypeptide sequence derived from an immunoglobulin able to bind with an antigen. Antibody as herein used includes polyclonal or monoclonal, multiple or single chain antibodies as well as immunoglobulins, whether deriving from natural or recombinant source.

An antibody-derived targeting domain can be a fragment of an antibody or a genetically engineered product of one or more fragments of the antibody, which fragment is involved in binding with the antigen. Examples include a variable region (Fv), a complementarity determining region (CDR), a Fab, a single chain antibody (scFv), a heavy chain variable region (VH), a light chain variable region (VL) and a camelid antibody (VHH).

In a preferred embodiment, the binding domain is a single chain antibody (scFv). The scFv may be murine, human or humanized scFv.

In a preferred embodiment the target antigen is a tumour antigen.

As used herein the term tumour antigen includes antigens expressed on tumour cells including biomarkers or cell surface markers that are found on tumour cells and are not substantially found on normal tissues or restricted in their expression in non-vital normal tissues.

In a preferred embodiment the CAR used in the method of the invention is targeted to the Cd44v6 tumor antigen.

In a further preferred embodiment, the antigen specific targeting domain in the CAR of the method of the invention is an anti-CD44v6 scFv. The anti-CD44v6 scFv may be derived from the anti-CD44v6 antibodies disclosed in US 6'972'324.

Spacer Domain

The CAR to be used in the method of the invention comprises an extracellular spacer domain that connects the antigen-specific targeting domain to the transmembrane domain. The most common sequence used as spacer is the constant immunoglobulin IgG1 hinge-CH2-CH3 Fc domain. Mutants and or variants of this spacer are disclosed in the art for example Hombach et al. 2010 Gene Ther. 17:1206-1213 disclose a spacer in which CH2 and CH3 domains of human IgG1 modified with the pva/a mutations to reduce Fc Receptor binding.

In a preferred embodiment, the spacer of the CAR used in the method of the invention is a fragment derived from the extracellular domain of human low affinity nerve growth factor (LNGFR) as disclosed in WO 2016/042461. Among the possible sequences falling within this genus, WO 2016/042461 discloses four specific species: (i) the entire extracellular domain of LNGFR (i.e.: including the four TNFR-Cys domains and the serine threonine rich stalk); (ii) a mutated version of the entire extracellular domain of LNGFR (such mutation consisting of the deletion of a fragment of the fourth TNFR-Cys domain substituted by three specific aminoacids); (iii) a fragment including only the four TNFR-Cys domains of the extracellular domain of LNGFR; (iv) a fragment including the first three TNFR-Cys domains of the extracellular domain of LNGFR and a mutated version of the fourth (such mutation consisting of the deletion of a fragment of the fourth TNFR-Cys domain substituted by three specific aminoacids).

LNGFR is not expressed on the majority of human hematopoietic cells, therefore, spacer units deriving from LNGFR can be used to facilitate selection of cells genetically engineered to express CARs and quantitative analysis of transduced gene expression by immunofluorescence. In a further aspect of the present invention, the first phase on the manufacturing method may further comprises, after transduction, a step of immunomagnetic selection of CAR-CD34+ stem cells. For example, after the end of the transduction step, the cells may be incubated with an antibody conjugated to magnetic beads and able to recognize the LNGFR derived spacer thus allowing purification of CAR-CD34+ stem cells using magnetic columns.

Examples of LNGFR derived spacer are reported below:

```
Spacer LNGFR wild-type long (NWL):
Protein sequence (SEQ ID NO: 1):
KEACPTGLYTHSGECCKACNLGEGVAQPCGANQTVCEPCLDSVTFSDVV
SATEPCKPCTECVGLQSMSAPCVEADDAVCRCAYGYYQDETTGRCEACR
VCEAGSGLVFSCQDKQNTVCEECPDGTYSDEANHVDPCLPCTVCEDTER
QLRECTRWADAECEEIPGRWITRSTPPEGSDSTAPSTQEPEAPPEQDLI
ASTVAGVVTTVMGSSQPVVTRGTTDN.

Nucleotide sequence (SEQ ID NO: 2):
AAAGAGGCCTGCCCCACCGGCCTGTACACCCACAGCGGAGAGTGCTGCA
AGGCCTGCAACCTGGGAGAGGGCGTGGCCCAGCCTTGCGGCGCCAATCA
GACCGTGTGCGAGCCCTGCCTGGACAGCGTGACCTTCAGCGACGTGGTG
TCCGCCACCGAGCCCTGCAAGCCTTGCACCGAGTGTGTGGGCCTGCAGA
GCATGAGCGCCCCCTGCGTGGAAGCCGACGACGCCGTGTGTAGATGCGC
CTACGGCTACTACCAGGACGAGACAACCGGCAGATGCGAGGCCTGTAGA
GTGTGCGAGGCCGGCAGCGGCCTGGTGTTCAGTTGTCAAGACAAGCAGA
ATACCGTGTGTGAAGAGTGCCCCGACGGCACCTACAGCGACGAGGCCAA
CCACGTGGACCCCTGCCTGCCCTGCACTGTGTGCGAGGACACCGAGCGG
CAGCTGCGCGAGTGCACAAGATGGGCCGACGCCGAGTGCGAAGAGATCC
CCGGCAGATGGATCACCAGAAGCACCCCCCCTGAGGGCAGCGACAGCAC
CGCCCCTAGCACCCAGGAACCTGAGGCCCCTCCCGAGCAGGACCTGATC
GCCTCTACAGTGGCCGGCGTGGTGACAACCGTGATGGGCAGCTCTCAGC
CCGTGGTGACACGGGGCACCACCGACAAT.

Spacer LNGFR wild-type short (NWS):
Protein sequence (SEQ ID NO: 3):
KEACPTGLYTHSGECCKACNLGEGVAQPCGANQTVCEPCLDSVTFSDVV
SATEPCKPCTECVGLQSMSAPCVEADDAVCRCAYGYYQDETTGRCEACR
VCEAGSGLVFSCQDKQNTVCEECPDGTYSDEANHVDPCLPCTVCEDTER
QLRECTRWADAECEE.

Nucleotide sequence (SEQ ID NO: 4):
AAAGAGGCCTGCCCCACCGGCCTGTACACCCACAGCGGAGAGTGCTGCA
AGGCCTGCAACCTGGGAGAGGGCGTGGCCCAGCCTTGCGGCGCCAATCA
GACCGTGTGCGAGCCCTGCCTGGACAGCGTGACCTTCAGCGACGTGGTG
TCCGCCACCGAGCCCTGCAAGCCTTGCACCGAGTGTGTGGGCCTGCAGA
GCATGAGCGCCCCCTGCGTGGAAGCCGACGACGCCGTGTGTAGATGCGC
CTACGGCTACTACCAGGACGAGACAACCGGCAGATGCGAGGCCTGTAGA
GTGTGCGAGGCCGGCAGCGGCCTGGTGTTCAGTTGTCAGGACAAGCAGA
ACACCGTGTGTGAAGAGTGCCCCGACGGCACCTACAGCGACGAGGCCAA
CCACGTGGACCCCTGCCTGCCCTGCACTGTGTGCGAGGACACCGAGCGG
CAGCTGCGCGAGTGCACAAGATGGGCCGACGCCGAGTGCGAGGAA.

Spacer LNGFR mutated long (NML):
Protein sequence (SEQ ID NO: 5):
KEACPTGLYTHSGECCKACNLGEGVAQPCGANQTVCEPCLDSVTFSDVV
SATEPCKPCTECVGLQSMSAPCVEADDAVCRCAYGYYQDETTGRCEACR
VCEAGSGLVFSCQDKQNTVCEECPDGTYSDEAARAADAECEEIPGRWIT
RSTPPEGSDSTAPSTQEPEAPPEQDLIASTVAGVVTTVMGSSQPVVTRG
TTDN.
```

-continued

Nucleotide sequence (SEQ ID NO: 6):
AAAGAGGCCTGCCCCACCGGCCTGTACACCCACAGCGGAGAGTGCTGCA
AGGCCTGCAACCTGGGAGAGGGCGTGGCCCAGCCTTGCGGCGCCAATCA
GACCGTGTGCGAGCCCTGCCTGGACAGCGTGACCTTCAGCGACGTGGTG
TCCGCCACCGAGCCCTGCAAGCCTTGCACCGAGTGTGTGGGCCTGCAGA
GCATGAGCGCCCCCTGCGTGGAAGCCGACGACGCCGTGTGTAGATGCGC
CTACGGCTACTACCAGGACGAGACAACCGGCAGATGCGAGGCCTGTAGA
GTGTGCGAGGCCGGCAGCGGCCTGGTGTTCAGTTGTCAAGACAAGCAGA
ATACCGTGTGTGAAGAGTGCCCCGACGGCACCTACAGCGACGAAGCCGC
CAGAGCCGCCGACGCCGAGTGCGAAGAGATCCCCGGCAGATGGATCACC
AGAAGCACCCCCCCTGAGGGCAGCGACAGCACCGCCCCTAGCACCCAGG
AACCTGAGGCCCCTCCCGAGCAGGACCTGATCGCCTCTACAGTGGCCGG
CGTGGTGACAACCGTGATGGGCAGCTCTCAGCCCGTGGTGACACGGGGC
ACCACCGACAAT.

Spacer LNGFR mutated short (NMS):
Protein sequence (SEQ ID NO: 7):
KEACPTGLYTHSGECCKACNLGEGVAQPCGANQTVCEPCLDSVTFSDVV
SATEPCKPCTECVGLQSMSAPCVEADDAVCRCAYGYYQDETTGRCEACR
VCEAGSGLVFSCQDKQNTVCEECPDGTYSDEAARAADAECEE.

Nucleotide sequence (SEQ ID NO: 8):
AAAGAGGCCTGCCCCACCGGCCTGTACACCCACAGCGGAGAGTGCTGCA
AGGCCTGCAACCTGGGAGAGGGCGTGGCCCAGCCTTGCGGCGCCAATCA
GACCGTGTGCGAGCCCTGCCTGGACAGCGTGACCTTCAGCGACGTGGTG
TCCGCCACCGAGCCCTGCAAGCCTTGCACCGAGTGTGTGGGCCTGCAGA
GCATGAGCGCCCCCTGCGTGGAAGCCGACGACGCCGTGTGTAGATGCGC
CTACGGCTACTACCAGGACGAGACAACCGGCAGATGCGAGGCCTGTAGA
GTGTGCGAGGCCGGCAGCGGCCTGGTGTTCAGTTGTCAGGACAAGCAGA
ACACCGTGTGTGAAGAGTGCCCCGACGGCACCTACAGCGACGAGGCCGC
CCGGGCCGCCGACGCCGAGTGCGAGGAA.

Transmembrane Domain

The CAR to be used in the method of the invention comprises a transmembrane domain between the spacer domain and the signaling domain. The transmembrane domain may be derived either from a natural or from a synthetic source. The domain deriving from natural sources may comprise the transmembrane sequence from any membrane-bound or transmembrane protein including any of the type I, type II or type III transmembrane proteins. Transmembrane regions that may be used in the CAR may be derived from the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD244 (2B4), DAP10 or DAP12. The domain deriving from synthetic source will comprise predominantly hydrophobic sequence including residues such as leucine and valine.

Prior art discloses examples of transmembrane domain that can be used in a CAR such as: 1) the CD28 TM region (Pule et al, *Mol Ther,* 2005, November; 12(5):933-41; Brentjens et al, CCR, 2007, Sep. 15; 13(18 Pt 1):5426-35; Casucci et al, *Blood,* 2013, Nov. 14; 122(20):3461-72.); 2) the OX40 TM region (Pule et al, *Mol Ther,* 2005, November; 12(5):933-41); 3) the 41BB™ region (Brentjens et al, *CCR,* 2007, Sep. 15; 13(18 Pt 1):5426-35); 4) the CD3 zeta™ region (Pule et al, *Mol Ther,* 2005, Nov; 12(5):933-41; Savoldo B, *Blood,* 2009, Jun. 18; 113(25):6392-402.); 5) the CD8a TM region (Maher et al, *Nat Biotechnol,* 2002, January; 20(1):70-5.; Imai C, *Leukemia,* 2004, April; 18(4): 676-84; Brentjens et al, CCR, 2007, Sep. 15; 13(18 Pt 1):5426-35; Milone et al, *Mol Ther,* 2009, August; 17(8): 1453-64).

Further examples of transmembrane domain may be applied by the skilled in the art to the CAR to be used in the method of the present invention.

In one embodiment the CAR used in the method of the invention comprises a transmembrane domain selected from any one or more of a transmembrane domain of a zeta chain of a T cell receptor complex, CD28, CD8a, CD4 or combinations thereof. Preferably the transmembrane domain is derived from CD28.

More preferably the transmembrane domain of CD28 consists of sequence (SEQ ID NO: 9)
FWVLVVVGGVLACYSLLVTVAFIIFWV In one embodiment the transmembrane and intracellular signaling domain comprises at least 85, 90, 95, 97, 98 or 99% identity to SEQ ID NO:9.

Co-Stimulatory Domain

The CAR used in the method of the present invention may include, in the cytoplasmic tail, one or more co-stimulatory domains. Such domains may consist of the intracellular signaling domain of one or more co-stimulatory protein receptors (e.g., CD28, 41BB, ICOS). The function of the co-stimulatory domain is to provide additional signals to the cells thus enhancing cell expansion, cell survival and development of memory cells.

The CAR used in the method of the present invention may comprise one or more co-stimulatory domain selected from the group consisting of the intracellular domain of members of the TNFR super family, CD28, CD137 (4-11B), CD134 (OX40), DaplO, CD27, CD2, CD5, ICAM-1, LFA-1, Lck, TNFR-1, TNFR-II, Fas, CD30, CD40, CD244 (2B4), DAP10, DAP12 or combinations thereof. Further examples of co-stimulatory domains may be employed by the skilled in the art in the CAR.

In one embodiment the costimulatory domain is derived from the intracellular domain of CD28

In a preferred embodiment the transmembrane and costimulatory domains are both derived from CD28. In one embodiment the transmembrane and intracellular costimulatory domain comprise the sequence below:

Transmembrane and Intracellular Portion of the Human CD28 (UNIPROT: P10747, CD28_HUMAN, Position 153-220)

(SEQ ID NO: 10)
FWVLVVVGGVLACYSLLVTVAFIIFWVRSKRSRLLHSDYMNMTPRRPGP
TRKHYQPYAPPRDFAAYRS

In one embodiment the transmembrane and costimulatory domains comprises at least 85, 90, 95, 97, 98 or 99% identity to SEQ ID NO: 10.

In one embodiment the intracellular costimulatory domain of the CAR is derived from the intracellular domain of CD28 and comprises the sequence (SEQ ID NO: 11)
RSKRSRLLHSDYMNMTPRRPGPTRKHYQPYAPPRDFAAYRS.

Intracellular Signaling Domain

The CAR used in the method of the invention may also comprise an intracellular signaling domain. This domain may be cytoplasmic, transmits the activation signal and direct the cell to perform its specialized function. Examples of intracellular signaling domains include, but are not limited to, ξ chain of the T-cell receptor or any of its homologs (e.g., η chain, FcεP1γ and β chains, MB1 (Igα) chain, B29 (Igβ) chain, etc.), CD3 polypeptides (Δ, δ and ε), syk family tyrosine kinases (Syk, ZAP 70, etc.), src family tyrosine kinases (Lck, Fyn, Lyn, etc.) and other molecules involved in T-cell signal transduction, such as CD2, CD5 and CD28.

The intracellular signaling domain may be human CD3 zeta chain, FcyRIII, FcsRI, cytoplasmic tails of Fc receptors, immunoreceptor tyrosine-based activation motif (ITAM) bearing cytoplasmic receptors or combinations thereof.

In a preferred embodiment signaling domain comprises the intracellular signaling domain of human CD3 zeta chain.

In one embodiment the intracellular signaling domain of human CD3 zeta chain comprises the following sequence: UNIPROT: P20963, CD3Z HUMAN, Position 31-143

(SEQ ID NO: 12)
RVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTAT

KDTYDALHMQALPPR

In one embodiment, the intracellular signaling domain comprises at least 85, 90, 95, 97, 98 or 99% identity to SEQ ID NO:12.

Additional intracellular signaling domains will be apparent to those of skill in the art and may be used in connection with alternate embodiments of the invention.

Polynucleotides

The term polynucleotide as used herein is defined as a polymer of nucleotides, which form a DNA or RNA fragment. One skilled in the art has the general knowledge that the 64 codons of the eukaryotic genetic code encode for only the 20 naturally-occurring amino acids and 3 stop codons, rendering the genetic code degenerate with respect to the encoding of amino acid residues. In view of the degeneracy of the genetic code, different polynucleotide sequences may encode the same polypeptide. By applying routine technique, it is possible to elaborate different polypeptide sequences that contain nucleotide substitutions and still encode for the polypeptide of the invention. Methods to modify polynucleotides are known in the art and may be applied by the skilled man in order to improve the polypeptide's activity or stability, or to avoid splicing phenomenon. Polynucleotides of the invention may be obtained by any means available in the art, including, without limitation, recombinant means, i.e. the cloning of nucleic acid sequences from a recombinant library or a cell genome, using ordinary cloning technology, PCR™, and the like, and by synthetic means. The polynucleotides used in the present invention may be codon-optimised. Codon optimization is a technique known in the art (WO 1999/41397 and WO 2001/79518) aimed to increase or decrease the protein expression in a cell of interest. Multiple codons can often code for the same amino acid, but the preferential use of codons is different in each organism. Therefore, in each organism, t-RNAs corresponding to certain codons are more abundant than others. A polynucleotide may be synthetized or modified to increase protein expression in a host cell, by using codons matching with the most abundant degenerate tRNAs without affecting the amino acid sequence of the protein.

Lentiviral Vector

In a preferred embodiment, the vector to be used in present invention is a lentiviral vector. A lentiviral vector as used herein refers to a genus within the family of retroviral vectors. Lentiviral vectors have a unique property among the retroviral vectors since they are able to infect non dividing cells. Lentiviral vectors offer the means to achieve significant levels of gene transfer in vivo.

A detailed list of lentiviruses may be found in Coffin et al ("Retroviruses" 1997 Cold Spring Harbour Laboratory Press Eds: J M Coffin, SM Hughes, HE Varmus pp 758-763). In brief, lentiviruses can be divided into primate and non-primate groups. Examples of primate lentiviruses include but are not limited to: the human immunodeficiency virus (HIV), the causative agent of human acquired-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV). In a preferred embodiment, the lentiviral vector is derived from an HIV lentivirus, more preferably the lentiviral vector is derived from an HIV-1 lentivirus.

An exemplary lentiviral vector to be used in the method of the of the invention comprises at least the following portion of lentiviral genome: a) a 5' long terminal repeat (LTR); b) the packaging sequence psi; c) a Rev Response Element (RRE); d) a promoter operably linked to a gene of interest; e) a 3' long terminal repeat (LTR). In a preferred embodiment the U3 region of the 5' LTR is replaced with a heterologous promoter selected from the group consisting of: a cytomegalovirus (CMV) promoter, a Rous Sarcoma Virus (RSV) promoter, or a Simian Virus 40 (SV40); thus rendering lentiviral transcription tat independent. In a further preferred embodiment the 3' LTR sequence contains a deletion of the U3 region (i.e. the vector is a self inactivating vector or SIN vector). The lentiviral vector may further comprise a lentiviral central polypurine tract (cPPT) and Woodchuck Hepatitis Virus (WHP) Posttranscriptional Regulatory Element (WPRE)).

A further exemplary lentiviral vector for use in the present invention is the vector described in Amendola et al, *Nat Biotechnol*. 2005 January; 23(1):108-16 that includes a bidirectional promoter for the expression of two coding sequences in opposite orientation, thus enabling efficient dual gene transfer. The bidirectional promoter is composed by minimal core promoter elements from the human cytomegalovirus (mCMV), joined upstream and in opposite orientation, to an efficient promoter derived from the human phosphoglycerate kinase (PGK) or polyubiquitin UBI-C gene. This lentiviral vector incorporating the bidirectional promoter may be used to express a CAR and a suicide gene in one single construct. In a preferred aspect of the invention the suicide gene is the Herpes Simplex Virus Thymidine Kinase (HSV-TK), more preferably a no splicing variant of the HSV-TK gene such as those disclosed in WO 2005/123912. In a further preferred embodiment, the suicide gene is the HSV-TK Mut2 encoded by the following polynucleotide sequence:

(Sequence ID NO: 13)
atggcttcgtaccctgccatcaacacgcgtctgcgttcgaccaggctg cgcgttctcgcggccatagcaaccgacgtacggcgttgcgccctcgcc gcagcaagaagccacggaagtccgcctggagcagaaaatgcccacgcta ctgcgggtttatatagacggtcctcacgggatggggaaaaccaccacca cgcaactgctggtggccctgggttcgcgcgacgatatcgtctacgtacc cgagccgatgacttactggcaggtgctgggggcttccgagacaatcgcg aacatctacaccacacaacaccgcctcgaccagggcgagatatcggccg gggacgcggcggtggtaatgacaagcgcccagataacaatgggcatgcc

```
ttatgccgtgaccgacgccgttctggctcctcatgtcggggggaggct gggagttcacatgccccgccccggccctcaccctcatcttcgaccgcc atcccatcgccgccctcctgtgctacccggccgcgcgataccttatggg cagcatgacccccaggccgtgctggcgttcgtggccctcatcccgccg accttgcccggcacaaacatcgtgttggggggccttccggaggacagac acatcgaccgcctggccaaacgccagcgccccggcgagcggcttgacct ggctatgctggccgcgattcgccgcgtttacgggctgcttgccaatacg gtgcggtatctgcagggcggcgggtcgtggtgggaggattggggacagc tttcggggacggccgtgccgcccagggtgccgagcccagagcaacgc gggcccacgacccccatatcggggacacgttatttaccctgtttcgggcc cccgagttgctggccccaacggcgacctgtataacgtgtttgcctggg ccttggacgtcttggccaaacgcctccgtcccatgcacgtctttatcct ggattacgaccaatcgcccgccggctgccgggacgccctgctgcaactt acctccgggatggtccagacccacgtcaccacccaggctccataccga cgatctgcgacctggcgcgcacgtttgcccgggagatgggggaggctaa ctga.
```

In another aspect of the invention there is provided a lentiviral vector including a bidirectional promoter that allows the expression of a CAR and a cytokine able improve NK cells survival and proliferation in vivo. In a preferred embodiment the cytokine IL15 may be used to such extent.

Manufacturing of lentiviral vectors may be performed using transient or stable packaging systems. In transient systems the packaging cells (for example HEK293 cells or HEK293 T HEK293-SF, TE671, HT1080 or HeLa) are co-transfected at least with: a packaging plasmid encoding lentiviral Gag/Pol, a plasmid encoding the envelope protein of interest and the transfer plasmid carrying the essential lentiviral genome elements as disclose above and the gene of interest. In further transient systems lentiviral regulatory protein Rev may be expressed in trans on a fourth separate plasmid. Examples of suitable env genes include, but are not limited to VSV-G env, MLV 4070 env, RD 114 env, RD 114-TR, RD 114pro, baculovirus 5 GP64 env, GALV or envelope proteins derived from Measle virus. Co-transfection may be performed using methods well known in the art for example using calcium phosphate or commercially available formulations such as polyethylenimine (PEI) or Lipofectamine™ 2000CD. Stable packaging cell lines for production of lentiviral vectors are disclosed for example in WO 2012/028681, WO 2004/022761, Broussau et al. Mol. Ther. 2008; 16 (3), 500-507 or Throm et al. 2009 May 21; 113(21):5104-10.

Cells

The invention further provides a composition comprising CAR-NK cells obtainable by the method of the present invention. It was surprisingly found that condition applied for transduction of stem cells with lentiviral vectors carrying a Chimeric Antigen Receptors has impact on the nature and composition of the intermediate cellular population containing CAR-CD34+ stem cells as well as on the final cellular population containing CAR-NK cells, resulting from the expansion and differentiation phase. CAR-NK cells obtainable according to the method of the invention present a synergistic therapeutic effect between the NK-cells and the CAR. Such effect results to be stronger than that obtained with a different manufacturing method. Therefore, the invention further provides a composition comprising CAR-NK cells obtainable by the method of the present invention for use in medicine, more preferably for use in immunotherapy, in particular for the treatment of tumours and haematological malignancies.

The term "immunotherapy" denotes a treatment that uses certain parts of a person's immune system to fight diseases such as cancer. The parts of the immune system can be either from the person having the disease, but also from another person, called "donor", such as the case in the present invention. A composition for use according to the invention is preferably used in cell-based immunotherapy, wherein immune effector cells, derived from an autologous, non-haploidentical donor are administered to a recipient in need thereof.

This invention preferably uses cells that are generated with a GMP-compliant culture system for the generation of large batches of immune effector cells, e.g. from umbilical cord blood (UCB)-derived CD34+ progenitor cells, preferably without T cell contamination. It is advantageous to use such cells as they have higher conformity, making, e.g., regulatory processes much easier. At the same time, the present invention enables usage of such large batches of immune effector cells, because previously, individual batches had to be generated, based on the at least partial match with the envisaged recipient because of safety concerns. The present invention, however, shows that immune effector cells as defined by the invention, mismatched beyond being haploidentical are safe to use in immunotherapy and that they show efficacy.

Preferably, a composition for use according to the invention further comprises at least one excipient, such as for instance water for infusion, physiologic salt solution (0.9% NaCl), or a cell buffer, preferably consisting of a physiologic salt solution substituted with a protein component such as human serum albumin (HAS).

In order for a composition of the invention to be used, e.g. in non-haploidentical mismatched situation, it is preferred that the composition for use according to the invention is low on B-cell or a T-cell numbers to avoid graft versus host disease. In a preferred embodiment, a composition for use according to the invention does not result in graft versus host disease. Preferably, the composition comprises at not more than 5% T cells and not more than 5% B cells, more preferably not more than 2% T cells and not more than 2% B cells, most preferably less than 1% T cells and less than 1% B cells.

In a preferred embodiment, a composition for use according to the invention is provided, wherein the immune effector cell is, next to being positive for a CAR, positive for Neural Cell Adhesion Molecule (NCAM).

Neural cell adhesion molecule (NCAM), is a glycoprotein of Immunoglobulin (Ig) superfamily expressed on the surface of neurons, glia, skeletal muscle and natural killer cells. NCAM, also called CD56, has been implicated as having a role in cell-cell adhesion, neurite outgrowth, synaptic plasticity, and learning and memory. NCAM is preferably used to define the population of differentiated immune effector cells for use according to the invention and can be used to discriminate the infused effector cells from patient's natural killer cells in the peripheral blood. Preferably, the composition for use according to the invention comprises more than 90% CD56+ cells, more preferably more than 95% CD56+ cells, most preferably more than 98% CD56+ cells.

Typically, the composition of the invention comprises a plurality of cells. It is not necessary for all the cells in the composition to have the features and effects as defined by the invention. However, it is preferred to have at least a certain percentage of immune effector cells as defined in the invention in the composition for use according to the invention in order to have the right balance with regard to efficiency (during production) and efficacy (in the clinics). In a preferred embodiment, a composition for use according to invention is provided, wherein the composition comprises a plurality of cells, characterized in that 30-100%, preferably 30-90%, more preferably 30-80%, more preferably 30-70%, more preferably 30-60%, more preferably 30-50%, most preferably 30-40% of the plurality of cells is CAR-NK cell as defined by the invention. Preferably, the composition comprising a plurality of cells is characterized in that 40-100%, more preferably 50-100%, more preferably 60-100%, more preferably 70-100%, more preferably 80-100%, most preferably 90-100% of the plurality of cells is a CAR-NK cell as defined by the invention. Other preferred ranges of CAR-NK cells as defined by the invention within a composition for use according to the invention are: 40-90%, 50-90%, 60-90%, 70-90%, 80-90%, 40-80%, 50-80%, 60-80%, 40-70%, 40-60%, 50-60% or 40-50%. For production efficiency, a lower percentage of the CAR-NK cells as defined by the invention is desired, whereas on the other hand for clinical efficacy and for regulatory reasons a higher percentage of the CAR-NK cells as defined by the invention is desired.

It is preferred, from a regulatory perspective, but also from a perspective of efficiency, that a composition for use according to the invention is obtained from a single donor. Even more preferred is that a single donor provides more than one treatment dose, such that large scale batches can be produced, be cleared or certified, and used off-the-shelf at the moment a random individual must be treated with a composition for use according to the invention. In a preferred embodiment, a composition for a use according to invention is provided, wherein the plurality of cells are derived from cells obtained from a single donor. Preferably, the plurality of cells are derived from at least one of umbilical cord blood and bone marrow, as these are rich sources of CD34 positive stem and/or progenitor cells.

Because of the possibility to use off-the-shelf compositions comprising CAR-NK cells the composition for use according to the invention shifts cell adoptive therapy a step further from personalized medicine towards more generic medication as it is no longer necessary to search for individual donors to match individual recipient. This also has a beneficial impact on the costs of treatment.

With "off-the-shelf" as used herein is meant that such composition is prepared and stored for direct usage when needed. In particular a composition that is available "off-the-shelf" is not generated for one specific recipient but in general can be used for different recipients at different time points. The composition as defined by the invention can for instance be frozen and, when needed, thawed and used as defined by the invention. A composition as defined by the invention enables large scale production of GMP generated immune effector cells that can theoretically be provided within minutes when needed for any random recipient.

In one embodiment, the invention provides a composition comprising a CAR-NK cell, wherein the composition is generated ex vivo in a method for the manufacturing of a population of NK-cells, genetically modified with a Chimeric Antigen Receptor (CAR) comprising:

(i) A first phase of production of an intermediate cellular population containing CD34+ cells carrying at least one polynucleotide coding for a CAR according to the following steps:
 a) obtaining a biological starting sample selected from the group consisting of bone marrow, peripheral blood, placenta or umbilical cord blood,
 b) isolating hematopoietic stem cells from such biological sample,
 c) culturing the isolated hematopoietic stem cells in the presence of a culture medium I,
 d) transducing cultured stem cells by incubating such cells with a lentiviral vector carrying at least a polynucleotide coding for a CAR, thus obtaining an intermediate cellular population containing CAR-CD34+ stem cells, and
 e) optionally, culturing the intermediate cellular population containing CAR-CD34+ stem cells in culture medium I for at least one day, wherein culture medium I is a basic culture medium, comprising a collection of cytokines, wherein said collection of cytokines comprises Interleukin-7 and one or more of stem cell factor (SCF), flt-3Ligand (FLT-3L), thrombopoietin (TPO), and two or more of granulocyte-macrophage-colony-stimulating factor (GM-CSF), granulocyte-colony-stimulating factor (G-CSF), and interleukin-6 (IL-6), (ii) a second phase comprising:
 an optional, preliminary step of further expanding the intermediate cellular population containing CAR-CD34+ stem cells from the first phase in culture medium II, thereby obtaining a cellular population containing CAR-CD34+ stem cells and CAR-NK progenitor cells, wherein culture medium II is a basic culture medium comprising a collection of cytokines, wherein said collection of cytokines comprises two or more of SCF, FLT-3L interleukin-15 (IL-15) and IL-7 and two or more of GM-CSF, G-CSF, and IL6, and
 a step of expanding and differentiating the intermediate cellular population from phase I containing CAR-CD34+ stem cells or the cellular population from the optional preliminary step containing CAR-CD34+ stem cells and CAR-NK progenitor cells into a cellular population containing CAR-NK cells, the step comprising culturing the intermediate cellular population from phase I containing CAR-CD34+ stem cells or the cellular population from the optional preliminary step containing CAR-CD34+ stem cells and CAR-NK progenitor cells in culture medium III, thereby obtaining a cellular population containing NK-cells wherein the culture medium III is a basic culture medium comprising a collection of cytokines, wherein said collection of cytokines comprises two or more of SCF, IL-7, IL-15 and interleukin-2 (IL-2) and two or more of GM-CSF, G-CSF, and IL-6.

A sample comprising hematopoietic stem and/or progenitor cells may be obtained in any possible way, such as for instance obtain or collect a stem and/or progenitor containing cell source, such as bone marrow, cord blood, placental material, peripheral blood, peripheral blood of a person treated with stem cell mobilizing agents, generated ex vivo from embryonic stem cells or any deviates thereof using cell culturing steps or generated ex vivo from induced pluripotent stem cells and any deviates thereof using cell culturing steps. Hematopoietic stem and/or progenitor cells can be further purified from such stem and/or progenitor containing cell sources using affinity purification methods.

With the term "ex vivo" is meant that the process or method performed is not used within a living individual, but for instance in a device able to culture cells, preferably an open or a closed cell culture device, such as a culture flask, a disposable bag or a bioreactor.

With the term "CD34+ stem cell" is meant a multipotent stem cell, which expresses the CD34 antigen on the cell surface, preferably being a stem cell, which is able to develop in all certain types of blood cells and more preferably a cell, which can give rise to lineage specific progenitor cells of the blood lineages.

With the term "CD34+ progenitor cell" is meant a multipotent progenitor cell, which expresses the CD34 antigen on the cell surface, preferably being a progenitor cell, which is able to develop in various types of blood cells and more preferably a cell, which can give rise to lineage specific progenitor cells of the certain blood lineages.

With the term "affinity purification" as used herein is meant, that the cells to be purified are labelled, by targeting for instance a specific epitope of interest for separation purposes, for instance targeting an antigen with an antibody coupled to an agent suitable for detection by a method for separation, using for instance antibodies coupled to fluorochromes for purification methods such as fluorescence activated cell sorting (FACS), and/or using for instance antibodies coupled to magnetic particles for magnetic selection procedures. Affinity purification methods are known in the art and can for instance be any method of separating biochemical mixtures based on a highly specific interaction such as that between antigen and antibody, enzyme and substrate, or receptor and ligand.

With the term "expanding" as used herein is meant multiplication of cells due to cell division events caused by a cell culturing step, preferably without essentially changing the phenotype of the cell, which is generally called "differentiation". With the phrase "without essentially changing the phenotype of the cell" is meant that the cell preferably does not change its function, its cell surface markers and/or its morphology.

With the term "differentiating" as used herein is meant changing the phenotype of the cell, which means changing the expression of certain surface molecules during the cell culture process, changing the cells function and/or changing the morphology of the cell, wherein the cell preferably still can expand due to the addition of cell culture medium. As indicated previously, the inventors have shown that a composition for use immunotherapy as defined by the invention is particularly useful for the treatment of a tumour. According to a preferred embodiment, the composition for use according to the invention is for the treatment of a tumour. Tumour, within the meaning of the invention, includes hematopoietic tumours or solid tumours. The tumour can either be malign or benign.

A composition for use in immunotherapy according to the invention can be used at different stages in the treatment of tumours, in particular in the treatment of hematopoietic tumours, such as e.g. acute myelogenous leukaemia (AML). For instance, as exemplified by the current invention, the composition can preferably be used as consolidation therapy in those (elderly) patients not eligible to undergo a bone marrow transplant. Additionally, as shown by others using another treatment, immune effector cell therapy according to the invention can preferably be used for patients not reaching complete remission on induction therapy (refractory patients), or those relapsing shortly after induction therapy (recurrent patients). Incorporation of immune effector cell therapy into other consolidation therapies is also feasible and preferred, such as the additional use of immune effector cells as defined by the invention in allogeneic HSTC regimens.

In a preferred embodiment, a composition for a use according to the invention is provided, wherein the composition to be administered in one treatment comprises at least $5 \times 10^5$ cells and not more than $5 \times 10^{11}$ cells.

The composition of the invention can be administered through any acceptable method, provided the immune effector cells are able to reach their target in the individual. It is for instance possible to administer the composition of the invention via the intravenous route or via a topical route, including but not limited to the ocular, dermal, pulmonary, buccal and intranasal route. With topical route, as used herein, is also meant any direct local administration such as for instance in the bone marrow, but also directly injected in, e.g., a solid tumour. In particular cases, e.g. if the immunotherapy is aimed at an effect on the mucosal layer of the gastrointestinal tract, the oral route can be used.

Preferably, a composition for a use according to the invention is provided, wherein the composition is administered by intravenous route or by a topical route or by oral route or by any combination of the three routes. With the term "topical" as used herein is meant, that the immune effector cells are applied locally, preferably at the site of tumour, which can be localized in any anatomical site, more specifically the tumour can be localized in the bone marrow or any other organ. The composition for use according to the invention can be administered once, but if deemed necessary, the composition may be administered multiple times. These can be multiple times a day, a week or even a month. It is also possible to first await the clinical result of a first administration, e.g. an infusion and, if deemed necessary, give a second administration if the composition is not effective, and even a third, a fourth, and so on.

In one preferred embodiment, a composition for a use according to the invention for the treatment of a tumour is provided, wherein the tumour is a hematopoietic or lymphoid tumour or wherein tumour is a solid tumour.

With the term "haematological", "hematopoietic" or "lymphoid" tumour is meant, that these are tumours of the hematopoietic and lymphoid tissues. Hematopoietic and lymphoid malignancies are tumours that affect the blood, bone marrow, lymph, and lymphatic system.

In those cases that the tumour is a hematopoietic or lymphoid tumour, a composition for use according to the invention is provided, wherein the tumour is one or more of leukaemia, lymphoma, myelodysplastic syndrome or myeloma, preferably a leukaemia, lymphoma or myeloma selected from acute myelogenous leukaemia (AML), chronic myelogenous leukaemia (CML), acute T cell leukaemia, acute lymphoblastic leukaemia (ALL), chronic lymphocytic leukaemia (CLL), acute monocytic leukaemia (AMoL), mantle cells lymphoma (MCL), histiocytic lymphoma or multiple myeloma, preferably AML.

In those cases that the tumour is a solid tumour, a composition for use according to the invention is provided, wherein the tumour is one of malignant neoplasms or metastatic induced secondary tumours of adenocarcinoma, squamous cell carcinoma, adenosquamous carcinoma anaplastic carcinoma, large cell carcinoma or small cell carcinoma, hepatocellular carcinoma, hepatoblastoma, colon adenocarcinoma, renal cell carcinoma, renal cell adenocarcinoma, colorectal carcinoma, colorectal adenocarcinoma, glioblastoma, glioma, head and neck cancer, lung cancer, breast cancer, Merkel cell cancer, rhabdomyosarcoma, malignant melanoma, epidermoid carcinoma, lung carcinoma, renal carcinoma, kidney adenocarcinoma, breast carcinoma, breast adenocarcinoma, breast ductal carcinoma, non-small cell lung cancer, ovarian cancer, oral cancer, anal cancer, skin cancer, Ewing sarcoma, stomach cancer, urethral cancer, uterine cancer, uterine sarcoma, vaginal cancer, vulvar cancer, Wilms tumour, Waldenstrom macroglobulinemia, pancreas carcinoma, pancreas adenocarcinoma, cervix carcinoma, squamous cell carcinoma, medulloblastoma, prostate carcinoma, colon carcinoma, colon adenocarcinoma, transitional cell carcinoma, osteosarcoma, ductal carcinoma, large cell lung carcinoma, small cell lung carcinoma, ovary adenocarcinoma, ovary teratocarcinoma, bladder papilloma, neuroblastoma, glioblastoma multiforma, glioblastoma astrocytoma, epithelioid carcinoma, melanoma or retinoblastoma.

In a preferred embodiment, a composition for use according to the invention is provided, wherein the solid tumour is selected from malignant neoplasms or metastatic induced secondary tumours of cervical cancers selected from adenocarcinoma, squamous cell carcinoma, adenosquamous carcinoma, cervix carcinoma, small cell carcinoma, and melanoma. In another preferred embodiment, a composition for use according to the invention is provided, wherein the solid tumour is selected from malignant neoplasms or metastatic induced secondary tumours of colorectal cancers selected from adenocarcinoma, squamous cell carcinoma, colon adenocarcinoma, colorectal carcinoma, colorectal adenocarcinoma, colon carcinoma, and melanoma.

The composition of the invention has several advantages with respect to treatment options known to date. The composition of the invention is beneficial independent of HPV types, tumour histology, tumour EGFR expression and KRAS status. In addition to it, the immune effector cell of the invention also overcomes HLA-E, HLA-G and (IDO) inhibition, thus resulting in enhanced anti-tumour effects against tumours, especially against cervical cancers and colorectal cancers.

The term "Epidermal growth factor receptor" or EGFR as it is commonly described, refers to a cell surface protein widely expressed in almost all healthy tissues. The EGFR protein is encoded by transmembrane glycoprotein and is a member of the protein kinase family. Overexpression of EGFR and mutations in its downstream signalling pathway has been associated with bad prognosis in several solid tumours like colon, lung and cervix.

The term Kirsten rat sarcoma viral oncogene (KRAS) refers to the gene actively involved in regulating normal tissue signalling, part of EGFR downstream signalling pathway. However, mutations in the KRAS gene has been reported in tumour cells in solid tumours of colon, rectum and lungs. This activating mutations occurring in more than 50% of colorectal cancer patient helps tumour cells to evade EGFR targeting drugs like cetuximab and panitumumab.

The term "human papilloma virus (HPV) as used herein refers to the group of viruses which causes cervical cancer in women. HPV virus affects the skin and moist membranes surrounding mouth, throat, vulva, cervix and vagina. HPV infection causes abnormal cell changes that leads to cancer in the cervix.

The term Indoleamine 2,3 dioxygenase (IDO) as used herein refers to an enzyme which acts as a catalyst in degrading amino acids L-tryptophan to N-formylkynurenine. Overexpression of IDO commonly reported in solid tumours of prostate, gastric, ovarian, cervix and colon, enables tumour cells to evade killing by cytotoxic T cells and NK cells.

The invention is described in more detail in the following, non-limiting examples.

EXAMPLES

Example 1—Description of LNGFR-Spaced CD44v6 CAR

The CAR construct used in the examples is the CD44v6-NWL disclosed in WO 2016/042461 that includes detailed description of the sequences of such construct. cDNA encoding the CAR CD44v6-NWL was purchased from the originators.

A schematic version of the structure of the CAR construct CD44v6-NWL is shown in FIG. 1.

The CAR CD44v6-NWL consists of a CD44v6 binding domain, the LNGFR wild-type long spacer (including the four TNFR-Cys domains and the entire serine threonine rich stalk), the transmembrane and co-stimulatory domain of CD28 and the intracellular domain of CD3 □chain. The protein sequence of the CAR CD44v6-NWL is reported below (SEQUENCE ID NO 14):
MEAPAQLLFLLLLWLPDTTGEIVLTQSPATLSLSPGERATLSCSASSSI

NYIYWLQQKPGQAPRILIYLTSNLASGVPARFSGSGSGTDFTLTISSLE

PEDFAVYYCLQWSSNPLTFGGGTKVEIKRGGGGSGGGGSEVQLVESGGG

LVKPGGSLRLSCAASGFTFSSYDMSWVRQAPGKGLEWVSTISSGGSYTY

YLDSIKGRFTISRDNAKNSLYLQMNSLRAEDTAVYYCARQGLDYWGRGT

LVTVSSGDP*KEACPTGLYTHSGECCKACNLGEGVAQPCGANQTVCEPCL*

*DSVTESDVVSATEPCKPCTECVGLQSMSAPCVEADDAVCRCAYGYYQDE*

*TTGRCEACRVCEAGSGLVESCQDKQNTVCEEECPDGTYSDEANHVDPCLP*

*CTVCEDTERQLRECTRWADAECEEIPGRWITRSTPPEGSDSTAPSTQEP*

*EAPPEQDLIASTVAGVVTTVMGSSQPVVTRGTTDNPK*FWVLVVVGGVLA

CYSLLVTVAFIIFWVRSKRSRLLHSDYMNMTPRRPGPTRKHYQPYAPPR

DFAAYRS*RVKFSRSADAPAYQQGQNQLYNELNLGRREEYDVLDKRRGRD*

*PEMGGKPRRKNPQEGLYNELQKDKMAEAYSEIGMKGERRRGKGHDGLYQ*

*GLSTATKDTYDALHMQALPPR*

Legend
In Bold: CD44v6-Specific Single-Chain Fragment
In Italics Underlined: LNGFR Spacer
In Bold Underlined: CD28 Transmembrane and Costimulatory Domain
In Italics: CD3 Zeta-Chain Signaling Domain Example 2—Phase 1 Production of Intermediate CAR-CD34+ Stem Cellular Population The first phase of the method of the invention provides the conditions to produce an intermediate cellular population containing CD34+ stem cells carrying at least one polynucleotide coding for a CAR. Engineering of stem cells is obtained by transduction with a tat independent SIN lentiviral vector carrying an expression cassette containing the human Phosphoglycerate Kinase (hPGK) promoter to drive constitutive expression of the CAR CD44v6-NWL disclosed in Example 1.

The experiment consists in the transduction of CD34+ cells isolated from UCB using different conditions:

CONDITION A: A basal cell culture medium (Cell-Genix® GMP Stem Cell Growth Medium, obtained from Cellgenix GmbH, Freiburg, Germany) supplemented with cytokines (300 ng/ml Flt3-L and SCF, 100 ng/ml TPO and 60 ng/ml IL3). Condition A is a control method that applies transduction conditions others than those of the present invention. IDC-A3_Sub,AMD CONDITION B: A basal cell culture medium (Glycostem Basal Growth Medium (GBGM™ obtained from Glycostem Therapeutics, Oss, The Netherlands) supplemented with 10% human serum, cytokines (10 pg/ml GM-CSF, 250 pg/ml G-CSF, 50 pg/ml IL-6, 25 ng/ml SCF, 25 ng/ml Flt-3L, 25 ng/ml TPO, 25 ng/ml IL-7) and 20 µg/ml heparin.

Condition B is a representative example of the phase 1 of the method of the present invention.

The aim of the experiment is the identification of the most effective conditions to obtain an intermediate cellular population containing CAR-CD34+ stem cells to be expanded and differentiated into CAR-NK cells in the second phase of the manufacturing process. The complete experimental scheme is summarized below:

TABLE 1

Experimental conditions

| Sample description | Condition | Tot n. of cells | Vector |
| --- | --- | --- | --- |
| PDE_M17112 A TRA | Transduced under CONDITION A | 1.4 × 10⁶ cells | PDE_B17100 (LVV-CAR44v6) |
| PDE_M17112 B TRA | Transduced under CONDITION B | 1.4 × 10⁶ cells | |
| PDE_M17112 A NT | NT CONTROL OF CONDITION A | 1.1 × 10⁶ cells | Na |
| PDE_M17112 B NT | NT CONTROL OF CONDITION B | 1.1 × 10⁶ cells | |

The main steps for CD34+ transduction process are disclosed in table 2.

TABLE 2

Experimental procedure

| DAY | Process step |
| --- | --- |
| 0 | ➤ Purification of CD34⁺ cells from UCB |
| | ➤ Coating of plate with RetroNectin for transduced conditions (A, B) and mock conditions |
| | ➤ CD34⁺ cell seeding in RetroNectin-coated wells |
| 1 | ➤ First transduction run at MOI 100 for conditions A-B with LV-CAR vector |
| | ➤ Not-transduced cells treated as conditions A and B |
| 2 | ➤ Second transduction run at MOI 100 for conditions A and B with LV-CAR vector |
| | ➤ Not-transduced cells treated as conditions A and B |
| 3 | ➤ Conditions A |
| | ➤ End of transduction |
| | ➤ Centrifugation and resuspension for cryopreservation at 1 × 10⁶ cells/ml; |
| | ➤ Cells were frozen in controlled temperature rate freezer. |
| | ➤ Conditions B |
| | ➤ sampling for testing |
| | ➤ Split of the cells |
| 5 | ➤ Conditions B |
| | ➤ Split of the cells |
| 7 | ➤ Conditions B |
| | ➤ sampling for testing. |
| | ➤ Freezing of progenitor cells between 2-4 × 10⁶ cells/ml for each condition (≥0.5 ml/vial). Cells were frozen using controlled temperature rate freezer. |

2.2 Starting Biological Material

For the execution of the experiment, CD34+ cells were isolated from three Umbilical Cord Blood (UCB) provided by NHIS blood and Transplant (Table 3).

TABLE 3

UCB data

| Sample | Supplier | Lot |
| --- | --- | --- |
| UCB 1 | NHS blood | G18011710473970 |
| UCB 2 | and | G18011710808979 |
| UCB 3 | Transplant | G18011710473774 |

2.3 CD34 Isolation and Characterization

Three UCB (supplied by NHS blood and Transplant) were processed independently: mononuclear cells (MNCs) were isolated using manual density gradient with Lymphoprep™ according to standard conditions of the provider. Further, immunomagnetic selection was applied to each sample in order to obtain CD34+ purification: cells were first immune labelled with anti CD34 antibody conjugated to magnetic beads, and then loaded into Miltenyi LS MidiMACS columns according to the conditions of the provider.

Sample with higher purity in term of CD34+ cells 00 was chosen for the experiment and the other cells were frozen.

Cell number, viability and total process yield in terms of CD34+ cell recovery are reported in Table 4.

TABLE 4 cell number, viability and recovery

| Batch | WBCs (×10⁶) | % CD34⁺ cells in WBCs | Tot. CD34⁺ pre-manipulation (×10⁶) | Tot. viable cells after purification (×10⁶) | % CD34⁺ after purification | Tot. CD34⁺ after purification (×10⁶) | CD34⁺ recovery (%) | % Viable |
| --- | --- | --- | --- | --- | --- | --- | --- | --- |
| PDE_M17112 UCB 1 | 730 | 0.33 | 2.41 | 4.00 | 56.2 | 2.25 | 93 | 93 |

TABLE 4-continued cell number, viability and recovery

| Batch | WBCs (×10⁶) | % CD34⁺ cells in WBCs | Tot. CD34⁺ pre-manipulation (×10⁶) | Tot. viable cells after purification (×10⁶) | % CD34⁺ after purification | Tot. CD34⁺ after purification (×10⁶) | CD34⁺ recovery (%) | % Viable |
|---|---|---|---|---|---|---|---|---|
| PDE_M1 7112 UCB 2 | 1165 | 0.99 | 11.50 | 5.76 | 94.0 | 5.41 | 47 | 95 |
| PDE_M1 7112 UCB 3 | 739 | 0.86 | 6.36 | 3.55 | 83.6 | 2.97 | 47 | 91 |

CD34+ cells recovered from UCB 1 and UCB 3 were frozen in controlled temperature rate freezer.

Immunophenotype of UCB samples was evaluated by FACS analysis. The acquisition was performed on BD FACSCanto 2 and the data were analyzed using DIVA Software. Table 5 shows the results on pre-manipulation and negative fraction of UCB samples 1, 2 and 3 at day 0. Table 6 shows the results on positive fraction of UCB samples 1, 2 and 3 at day 0.

TABLE 5

Immunophenotype data of UCB pre-manipulation and negative fraction (NF)

| | DAY 0 | | | | | |
|---|---|---|---|---|---|---|
| | CB pre-man 1 | NF 1 | CB pre-man 2 | NF 2 | CB pre-man 3 | NF 3 |
| CD34 stem | 0.33 | 0.14 | 0.99 | 0.04 | 0.86 | 0.17 |
| CD34+/CD15−/CD19− | 98.0 | 99.5 | 96.8 | 94.3 | 97.0 | 96.5 |
| CD34+/CD19+ | 2.4 | 1.1 | 3.1 | 3.9 | 4.0 | 2.6 |
| CD34+/CD15+ | 0.0 | 0.0 | 1.3 | 3.9 | 0.6 | 1.6 |
| CD3 | 16.1 | 31.6 | 12.7 | 17.1 | 26.5 | 37.1 |
| CD16+/CD56+/CD3− | 3.5 | 4.3 | 8.7 | 6.3 | 1.5 | 1.3 |
| CD19 | 2.9 | 4.1 | 3.5 | 4.4 | 3.5 | 4.4 |
| CD15 | 68.6 | 44.6 | 67.0 | 60.7 | 57.5 | 41.5 |
| Viability (% 7AAD−) | 87.1 | 96.1 | 95.6 | 97.4 | 79.9 | 94.8 |

TABLE 6

Immunophenotype data of positive fraction

| | Day 0 | | |
|---|---|---|---|
| | PF 1 | PF 2* | PF 3 |
| | % on CD45 population | | |
| CD34 | 56.2 | 94.0 | 83.6 |
| CD34+/CD19+ | 1.7 | 3.2 | 3.8 |
| CD34−/CD19+ | 3.1 | 0.5 | 1.4 |
| CD34+/CD15+ | 12.1 | 7.9 | 22.7 |
| CD34−/CD15+ | 22.2 | 4.2 | 12.6 |
| CD16+/CD56+/CD3− | 15.1 | 1.6 | 2.8 |
| CD3 | 10.1 | 0.1 | 2.5 |
| | % on CD34 population | | |
| CD34+/CD15−/CD19− | 74.7 | 88.3 | 66.5 |
| CD34+/CD133+ | 6.0 | 73.5 | 37.9 |
| CD34+/CD90+ | 1.2 | 3.1 | 2.9 |

Positive Fraction from UCB Sample 2 was Chosen for Transduction 2.4 CD34+ Seeding After sampling for IF analysis and clonogenic assay, cells recovered from UCB 2 were seeded in non-tissue culture treated plates, previously coated with RetroNectin®, at seeding concentration of $1.0 \times 10^6$ cells/ml (Table 7).

2.5 CD34+ Transduction

On day 1, following 22h45' incubation, half of the cell suspensions were collected from plates, centrifuged and suspended with LV CAR-CD44v6 vector PDE_B 17100 (1st transduction run).

After 15 hour of incubation, cells were collected and counted and then centrifuged and suspended in medium 1× cytokines at seeding concentration of $1.0 \times 10^6$ cells/ml. The following equation was used to calculate growth rate of the culture:

$$\text{Growth rate} = \frac{\text{total viable cells number at passage } x}{\text{total viable cells number seeded at passage } (x-1)}$$

TABLE 7 cell concentration, viability and growth rate after 1st run of transduction (Day 2)

| Sample | Condition | Viable cells seeded/ml day 0 (×10⁶/ml) | Volume of cells seeded day 0 (ml) | Total cells seeded day 0 (×10⁶) | Viable cell concentration/ml day 2 (×10⁶/ml) | Total volume pre-count day 2 (ml) | Total viable cells day 2 (×10⁶) | Growth Rate total cells day 0-2 | % Viable |
|---|---|---|---|---|---|---|---|---|---|
| PDE_M171 12 A | Transd. Condition A | 1.0 | 1.4 | 1.44 | 0.79 | 2.2 | 1.74 | 1.2 | 99 |

TABLE 7-continued cell concentration, viability and growth rate after 1st run of transduction (Day 2)

| Sample | Condition | Viable cells seeded/ml day 0 (×10⁶/ml) | Volume of cells seeded day 0 (ml) | Total cells seeded day 0 (×10⁶) | Viable cell concentration/ml day 2 (×10⁶/ml) | Total volume pre-count day 2 (ml) | Total viable cells day 2 (×10⁶) | Growth Rate total cells day 0-2 | % Viable |
|---|---|---|---|---|---|---|---|---|---|
| PDE_M171 12 A NT | NT Condition A | 1.0 | 1.1 | 1.13 | 0.66 | 2.0 | 1.32 | 1.2 | 100 |
| PDE_M171 12 B | Transd. Condition B | 1.0 | 1.4 | 1.44 | 0.58 | 2.2 | 1.28 | 0.9 | 100 |
| PDE_M171 12 B NT | NT Condition B | 1.0 | 1.1 | 1.13 | 0.64 | 2.0 | 1.28 | 1.1 | 98 |

On day 3, cells were collected and counted.

The overall growth rate obtained from day 0 to day 3 (end of transduction) was also calculated by multiplying the individual growth rates.

TABLE 8 cell concentration, viability and growth rate after 2nd run of transduction (Day 3)

| Sample | Condition | Viable cells seeded/ml day 2 (×10⁶/ml) | Volume of cells seeded day 2 (ml) | Total cells seeded day 2 (×10⁶) | Viable cell conc./ml day 3 (×10⁶/ml) | Total volume day 3 (ml) | Total viable cells day 3 (×10⁶) | Growth Rate total cells day 2-3 | % Viable | Overall Growth rate day 0-3 |
|---|---|---|---|---|---|---|---|---|---|---|
| PDE_M17112 A | Transd. Cond. A | 1.1 | 1.4 | 1.58 | 1.08 | 2.8 | 3.02 | 1.9 | 100 | 2.3 |
| PDE_M17112 A NT | NT Cond. A | 1.0 | 1.2 | 1.19 | 1.02 | 2.4 | 2.45 | 2.1 | 100 | 2.4 |
| PDE_M17112 B | Transd. Cond. B | 1.0 | 1.2 | 1.16 | 1.28 | 2.2 | 2.82 | 2.4 | 99 | 2.2 |
| PDE_M17112 B NT | NT Cond. B | 1.0 | 1.2 | 1.15 | 0.96 | 2.2 | 2.11 | 1.8 | 100 | 2.1 |

At the end of transduction, cells of condition A were collected and transferred in a centrifuge tube; after one wash of the wells with CellGenix® GMP Stem Cell Growth Medium, the cells were centrifuged, suspended in fresh CellGenix® GMIP Stem Cell Growth Medium, counted and sampled for testing. Remaining cells were frozen in human serum+Glycostem Basal Medium 1400 DMSO (1:1) in cryovials.

Cells of condition B were collected, counted and sampled for testing as described in Table 6. Remaining cells were centrifuged and resuspended in medium 1× cytokines at seeding concentration of 0.4×10⁶ cells/ml.

At day 5, cells of condition B were counted and added 1 volume of fresh medium.

TABLE 9 cell concentration, viability and growth rate of sample B (day5)

| Sample | Condition | Viable cells seeded/ml (day 3) (×10⁶/ml) | Volume of cells seeded day 3 (ml) | Total cells seeded (day 3) (×10⁶) | Viable cell conc./ml (day 5) (×10⁶/ml) | Tot. vol. pre-count at day 5 (ml) | Total viable cells day 5 (×10⁶) | Growth Rate total cells (day 3-5) | % Viable |
|---|---|---|---|---|---|---|---|---|---|
| PDE_M17 112 B | Trans. cond. B | 0.4 | 4.2 | 1.66 | 1.57 | 4.1 | 6.44 | 3.9 | 98 |
| PDE_M17 112 B NT | NT Cond. B | 0.4 | 3.6 | 1.44 | 1.16 | 3.5 | 4.06 | 2.8 | 98 |

At day 7, cells of condition B were collected and transferred in a centrifuge tube; after one wash of the wells with Gly medium, the cells were centrifuged, resuspended in fresh Gly medium (using twofold the cell culture volume) for DS formulation, counted and sampled for testing as described in Table 6. Remaining cells were frozen in human serum+Gly medium 14% DMSO (1:1) in cryovials.

TABLE 10 cell concentration, viability and growth rate of sample B (day 7)

| Sample | Condition | Viable cells seeded/ml (day 5) ($\times 10^6$/ml) | Volume of cells seeded day 5 (ml) | Total cells seeded (day 5) ($\times 10^6$) | Viable cell conc./ml (day 7) ($\times 10^6$/ml) | Tot. volume pre-count at day 7 (ml) | Total viable cells day 7 ($\times 10^6$) | Growth Rate total cells (day 5-7) | % Viable | Overall Growth rate (day 0-7) |
|---|---|---|---|---|---|---|---|---|---|---|
| PDE_M1 7112 B | Trans. Cond. B | 0.8 | 8.0 | 6.28 | 1.36 | 12.5 | 17.0 | 2.7 | 96 | 22.7 |
| PDE_M1 7112 B NT | NT Cond. B | 0.6 | 6.8 | 3.94 | 1.29 | 11.8 | 15.2 | 3.9 | 98 | 22.6 |

The overall growth rate obtained from day 0 to day 7 was also calculated by multiplying the individual growth rates.

Immunophenotype was evaluated by FACS analysis. The acquisition was performed on BD FACSCanto 2 and the data were analyzed using DIVA Software. Cells were analyzed at day (condition A and condition B) and at day 7 (condition B).

TABLE 11

Immunophenotype data of transduced cells

| | Day 3 | | Day 7 |
|---|---|---|---|
| | PDE_M17112 A TRA | PDE_M17112 B TRA | PDE_M17112 B TRA |
| | % on CD45 population | | |
| CD34 | 99.4 | 96.6 | 40.0 |
| CD34+/CD19+ | 0.5 | 0.2 | 0.1 |
| CD34-/CD19+ | 0.0 | 0.2 | 0.2 |
| CD34+/CD15+ | 60.1 | 23.3 | 3.8 |
| CD34-/CD15+ | 0.6 | 2.8 | 36.6 |

TABLE 11-continued

Immunophenotype data of transduced cells

| | Day 3 | | Day 7 |
|---|---|---|---|
| | PDE_M17112 A TRA | PDE_M17112 B TRA | PDE_M17112 B TRA |
| CD16+/CD56+/CD3− | 0.8 | 0.7 | 3.3 |
| CD3 | 0.0 | 0.0 | 0.0 |
| | % on CD34 population | | |
| CD34+/CD15−/CD19− | 42.3 | 76.7 | 78.1 |
| CD34+/CD133+ | 63.6 | 57.1 | 17.3 |
| CD34+/CD90+ | 24.2 | 14.9 | 3.5 |

2.6 CD34+ Cells Clonogenic Capacity

Clonogenic capacity of hematopoietic progenitors, according to method disclosed in Pharmacopeia Monography EP 2.7.28 (Colony forming assay for human hematopoietic progenitor cells).

The analysis was performed at cell thawing (day 0) for basal clonogenic potential determination and at the end of transduction phase (day 3).

TABLE 12

Clonogenic capacity results at day 0
Results of Day 0 sample

| | Raw data of seeding concentrations and corresponding mean n ° of colonies for results determinations | | | | | | Clonogenic capacity/106 cells | | |
|---|---|---|---|---|---|---|---|---|---|
| Sample | plated cells | CFU-GM | BFU-E+ CFU-E | CFU-GEM | Total | % CV | CFU-GM | BFU-E+ CFU- | Total |
| PDE_M1 7112 | 250 | 18.67 | 24.67 | 1.33 | 44.67 | 3 | 7.47E+04 | 9.87E+04 | 1.79E+05 |

TABLE 13

Clonogenic capacity results at the end of transduction phase (Day 3)

Results of day 3 samples

| Batch Number | Id. Sample | Raw data of seeding concentrations and corresponding mean n° of colonies | | | | | | Clonogenic capacity/10⁶ cells | | | ratio |
|---|---|---|---|---|---|---|---|---|---|---|---|
| | | plated cells number | CFU-GM | BFU-E+ CFU-E | CFU-GEMM | Total | % CV | CFU-GM | BFU-E+ CFU-E | Total | day3/day0 |
| PDE_M17112 | A | 250 | 18.75 | 31.50 | 0.25 | 50.5 | 11 | 7.50E+04 | 1.26E+05 | 2.02E+05 | 1.1 |
| | B | 250 | 16.00 | 25.25 | 1.00 | 42.25 | 3 | 6.40E+04 | 1.01E+05 | 1.69E+05 | 0.9 |

2.6.1 Transduction Efficiency

Transduction efficiency was evaluated by FACS analysis for NGFR marker. Cells were analyzed after liquid culture and on colonies pool from clonogenic assay.

TABLE 14

Transduction efficiency after LC

| | AFTER 14 Days LC | |
|---|---|---|
| | PDE_M17112 A TRA | PDE_M17112 B TRA |
| NGFR | 45.5 | 17.0 |

TABLE 15

Transduction efficiency on colonies pool

| | | COLONIES POOL FROM CLONOGENIC ASSAY | |
|---|---|---|---|
| | | % su CD45+ | % su CD45− |
| PDE_M17112 A TRA | NGFR+ | 56.5 | 56.3 |
| PDE_M17112 B TRA | NGFR+ | 35.0 | 29.4 |

2.6.2 VCN Assays

Vector copy number was determined by quantitive PCR performed after 14 days myeloid culture of transduced CD34+ cells. The results are summarized in Table 16.

TABLE 16

VCN Results

| | LVV copies/cell After II Hit |
|---|---|
| PDE_M17112 A TRA | 1.4 |
| PDE_M17112 B TRA | 0.4 |

Conclusions

Cell Viability and Growth Rates:

The cells maintained a good viability during all the process (>96%) and the growth rate was similar among the two conditions.

Immunophenotype:

No differences in terms of stem cell characterization are arisen through analysis with the exception of the expression of CD15 marker that is higher in cells cultured and transduced according to condition A indicating a cellular population more committed to myeloid lineage. These phenotype is not observed in the cells cultured and transduced according to condition B i.e. the intermediate cellular population produced according to the method of the invention.

Clonogenic Capacity:

The clonogenic capacity of CD34+ cells at day 3 was analogous.

Transduction efficiency and Vector Copy Number:

Transduction efficiency and VCN are higher in condition A than in condition B.

Example 3—Phase 2 Cell Expansion and Differentiation of CAR-CD34+ Stem Cells into CAR-NK Cells 3.1 Thawing The cryopreserved CD44v6 transduced and MOCK progenitor cells from condition A (day 3) and B (day 7) were thawed in thawing buffer consisting of human serum albumin supplemented with 2.5 mM MgCl2 and 0.13 mg/ml DNAse. The CD34+ UCB cells were plated in tissue culture treated 6-wells plates in fresh expansion medium I at cell concentrations of $0.97 \times 10^6$ cells/ml (condition A); $2.11 \times 10^6$ cells/ml (condition B non T) and $1.99 \times 10^6$ cells/ml (condition B T).

The CD34+ UCB cells recovered well after the freeze-thaw cycle as depicted in table 17 showing the percentage viable cells from the total cells initially frozen.

TABLE 17

Reconstitution of progenitor cells day 3 (condition A) and 7 (condition B).

| Recovery % | B non T | B T | A non T | A T |
|---|---|---|---|---|
| After thawing | 62.76 | 56.63 | 85.92 | 78.31 |
| 3 (B) or 2 (A) days later | 360.35 | 295.35 | 310.68 | 264.09 |

3.2 Expansion Phase

Flowcytometry data for cell viability, CD34 content and LNGFR expression was measured in the expansion phase to monitor and provide optimal cell culture conditions. CD34+ UCB cells were cultured in fresh expansion medium I, a basal culture medium (GBGM) supplemented with 10% human serum, a low dose cytokine cocktail containing 10 pg/ml GM-CSF, 250 pg/ml G-CSF and 50 pg/ml IL-6; 25 ng/ml SCF, Flt-3L, TPO, IL-7 and 20 pg/ml heparin (Clivarin). Cells from condition A and B were cultured in expansion medium I till day 9, counted from day 4 (after thawing cells from condition A) and day 8 (cells from condition B). Expansion medium I was refreshed every 2-3 days a week. At day 10, the progenitor cells were cultured by adding expansion medium II, hereby replacing 25 mg/ml TPO for 20 ng/ml IL-15.

The real expansion in all the conditions was calculated starting from the day of thawing (expansion is set 1) at day 3 (condition A) or day 7 (condition B) and has shown no differences between condition B T and B non T. For condition A T and A non T, lower expansion was measured in A non T compared to A T. The theoretical expansion was calculated by excluding freeze-thaw effects on expansion, showing optimal expansion for all the conditions. Results from this comparison between all the conditions revealed lower expansion for the condition A, particularly A non T.

Results from the LNGFR expression showed natural CD271 expression in cells during the culture days 10 to 21.

3.3 Differentiation Phase

During differentiation the CD56 content as a marker of NK-cells was measured instead of the CD34 content alongside cell viability and LNGFR expression. Differentiation medium consists of GBGM supplemented with 2% human serum, a low dose cytokine cocktail containing 10 pg/ml GM-CSF, 250 μg/ml G-CSF and 50 pg/ml TL-6; 20 ng/ml SCF, IL-15, TL-7 and 1000 U/ml TL-2 (Proleukin). Differentiation medium was refreshed twice a week until end of culture.

The LNGFR expression in the CD44v6 transduced UCB-NK cells revealed high NGFR expression in condition A transduced NK-cells (87% at day 41) and mediate NGFR expression in condition B transduced NK-cells (37% at day 45).

Morphology results from the condition A CD44v6 transduced UCB-NK revealed enlarged cells in the culture compared to all the other conditions.

3.4 In Vitro Functionality Assay

An in vitro functionality assay was performed at the end of the culture with Mock and CD44v6 transduced UCB-NK cells from condition A and B against K562, T98G and THP-1 tumour cell lines respectively sensitive -, intermediate- and resistant to NK-cell cytotoxicity.

THP-1 human leukaemia monocytic cells were stimulated for 48h with 25 nM phorbol myristate acetate (PMA) at a cell density of $2\times10^5$ cells/ml and incubated for another 24 h with fresh culture medium to differentiate THP-1 cells in macrophages that are known to express CD44 (FIG. 4A). Target cells were labeled with 5 pM pacific blue succinimidyl ester (PBSE) at a concentration of $1\times10^6$ cells/ml for 10 minutes at 37° C. The target cells were washed in target culture medium and concentrated to $5\times10^5$ cells/ml. The NK-cells were concentrated to $5\times10^5$ cells/ml as well and cocultured with target cells (100 μl effectors+100 μl targets) in an overnight assay. For degranulation measurements anti-CD107a was added at the start of the incubation and anti-CD56 for NK-cell discrimination at the end of the incubation. Cytotoxicity was calculated based on flowcytometry read out for the apoptotic 7AAD viability marker for Effector:Target ratios of 1:1.

Lower cytotoxicity is observed for the CD44v6 transduced UCB-NK cells from condition A against the sensitive tumour cell line K562 compared to the other conditions.

3.5 Receptor Expression in NK-Cells

Mock and CD44v6 transduced UCB-NK cells from condition A at the end of the culture were screened for inhibiting (NKG2A) and activating (DNAM-1, NKG2C, NKG2D, CD16) receptor expression involved in NK-cell killing mechanisms (FIG. 5A).

Lower DNAM-1 activating receptor expression was measured for the CD44v6 transduced UCB-NK cells compared to the MOCK UCB-NK cells.

3.6 Shipment to MolMed

Fresh Mock and CD44v6 transduced UCB-NK cells from condition A (day 31) and B (day 35) were shipped to MolMed for further characterization of the functional activity and in vivo study with NSG mice. The remaining cells were frozen on day 34 (condition A) and 38 (condition B) in GBGM supplemented with 50% human serum and a final concentration of 7% DMSO to investigate the recovery of MOCK and CD44v6 transduced UCB-NK cells in regaining their functional capacity after thawing.

3.7 Reconstitution

Cryopreserved Mock and CD44v6 transduced UCB-NK cells from condition A (day 34) and B (day 38) were thawed in thawing buffer (described in 3.1) and after good recovery used in an in vitro functionality assay as described in 3.4.

Results from the in vitro functionality assay with Mock and CD44v6 transduced UCB-NK cells from condition A and B against the sensitive tumour cell line K562 show comparable results with the functionality data before reconstitution (FIG. 4B). Lower cytotoxicity is still observed for the CD44v6 transduced UCB-NK cell from condition A against K562.

Degranulation of the Mock and CD44v6 transduced UCB-NK cells, measured on the flowcytometer by the percentage CD107a+, were analyzed against the sensitive tumour cell line K562 (FIG. 4C).

For comparison of inhibiting and activating receptor expression involved in NK-cell killing mechanisms before and after reconstitution, Mock and CD44v6 transduced UCB-NK cells from condition A and B after reconstitution were screened for the same important NK-cells activating and inhibitory receptors with the addition of KIR2DL2/L3, KIR3DL and KIR2DL1 inhibitory receptors (FIG. 5B). After reconstitution, lower activating receptor expression of DNAM-1 and NKG2D was measured in the CD44v6 transduced UCB-NK cells from condition A.

Example 4—In Vitro Characterization of the Functional Activity of the MOCK NK and CAR-NK Cells To evaluate the antigen-specific activity of CD44v6-CAR NK cells, we performed a flow cytometry-based potency assay that measures degranulation and cytokines production in cells stimulated with target cell lines expressing or not expressing the CD44v6 antigen.

4.1 Experimental Design

Degranulation, as percentage of CD107a+ cells, and cytokine production, as percentage of TNF-α+ cells, were analyzed in mock NK and CD44v6-CAR NK produced under condition B (i.e. according to the method of the invention) and under condition A (i.e. control), at day 3 after the last medium change. As target cells, CD44v6 negative and positive tumour cells, both sensitive (K562, chronic myelogenous leukaemia) and resistant (MOLT-4, acute lymphoblastic leukaemia) to cytolysis by NK cells, were utilized at E:T ratio of 1:1. Moreover, effector cells were left untreated or stimulated with phorbol myristate acetate (PMA) and Ionomycin (IONO) to detect basal cell activation or unspecific-activation, respectively.

4.2 Materials

The potency test was performed in 96 well, round bottom plates, in a final volume of 100 µl.

The FACS analysis of effector cells was performed the panels of antibodies reported in Table 18.

TABLE 18

Antibody and Viability stain panel for NK cells staining

| Marker | Flourescence | Clone | Cat # | Company |
|---|---|---|---|---|
| CD271 | PE | HI100 | 557196 | BD |
| CD56 | PerCPCy5.5 | B159 | 560842 | BD |
| TNF-α | PE-Cy7 | MAb11 | 557647 | BD |
| CD107a | APC | H4A3 | 130-100-314 | Miltenyi |
| CD45 | APC H7 | 2D1 | 641417 | BD |
| Fixable Viability stain 510 | 510 | n.a. | 564406 | BD |

To generate CD44v6 positive K562 and MOLT-4 cell line, we performed transduction of the parental cell lines with a retroviral vector expressing CD44v6 antigen.

4.3 Results

Figure 2:
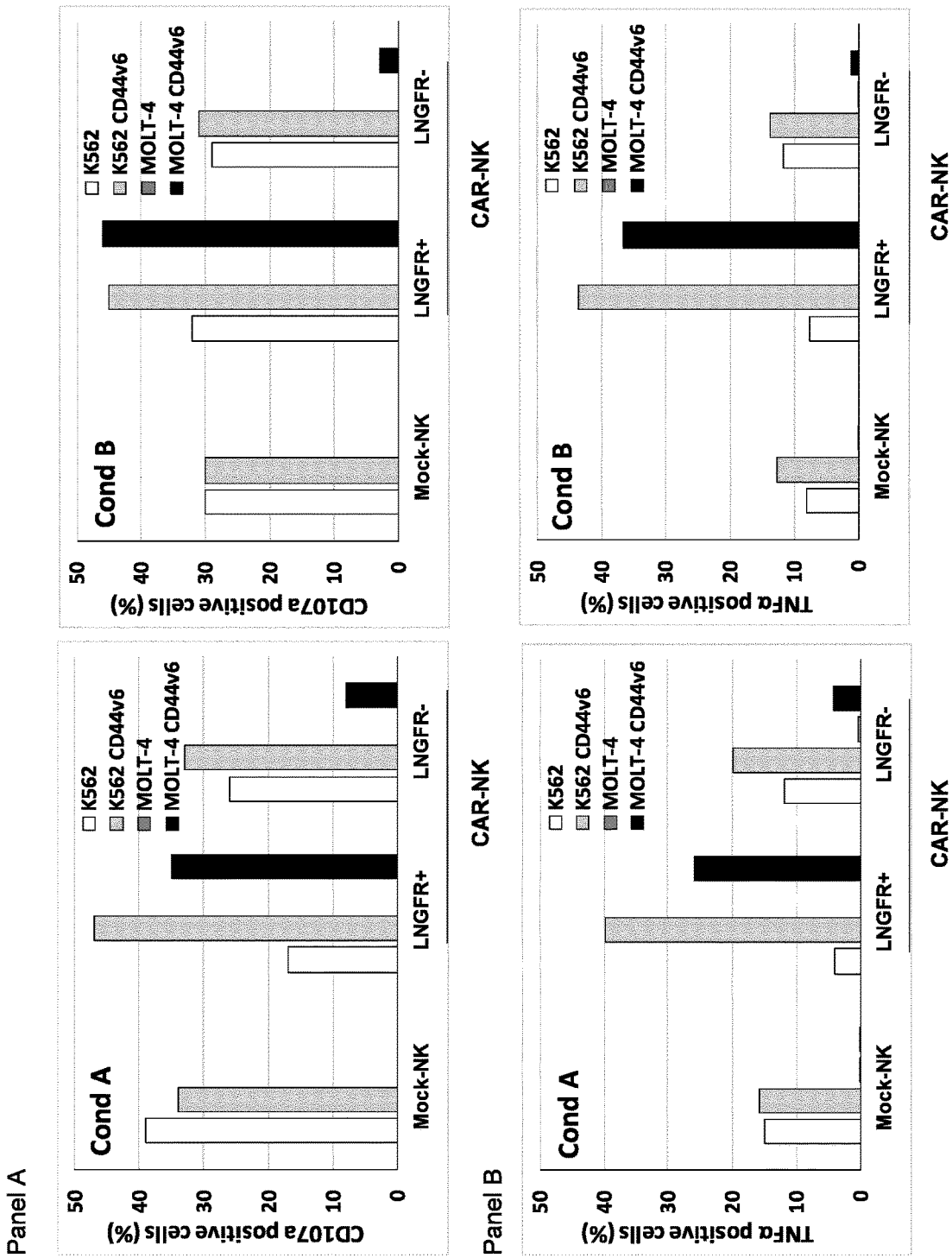
FIG. 2. in vitro functional activity of Mock NK and CD44v6-CAR NK cells obtained in condition A and condition B. the figure shows the frequency of CD107a positive cells (panel A; 18 hours) or TNF-α positive cells (panel B, 6 hours) for mock NK and CAR NK obtained under condition A (left) or condition B (right), stimulated with K562, MOLT-4, K562-CD44v6 or MOLT-4-CD44v6 cells. The analysis of CAR NK activity was performed in the two subpopulation, LNGFR+ cells and LNGFR− cells.

Mock NK and CD44v6-CAR NK obtained in condition A (control) and in condition B (i.e. according to the method of the invention) were tested for in vitro functional activity at day 38 of culture (condition A; 82% LNGFR+ cells) or at day 42 of culture (condition B; 33% LNGFR+ cells). All effectors and target cells were counted and resuspended in RPMI 1640 supplemented with human IgG, and incubated for 20 min on ice. After centrifugation, effector cells (0.2× $10^6$ cells/condition) were cultured in RPMI+10% FBS, alone or with the different target cell lines at E:T ratio of 1:1. Cells were stimulated with PMA/IONO as positive control for cells functionality. After 6 or 18 hours of incubation in the presence of CD107a Ab, brefeldin and/or monensin, NK were stained for surface antigens with the appropriate panel of fluorescent Abs, as reported in Table 18. Samples were then fixed and permeabilized, according to manufacturer's instruction for intracellular TNF-α staining, and analysed by flow cytometry. The percentages of viable positive effector cells stimulated with the different targets (after subtraction of the percentage of positive effector cells incubated alone) are shown in FIG. 2, panel A (percentage of CD107a positive cells at 18 hours), and panel B (percentage of TNF-α positive cells at 6 hours). The analysis of CAR NK activation was performed in the two subpopulation of LNGFR positive and negative cells. Both mock and transduced NK cells (both conditions A and B) recognize the NK-sensitive K562 cell lines, (although CD44v6-CAR NK cells from condition A show a functional decrease with respect to Mock-NK), but only the CAR-NK LNGFR+ cells show a clear, specific increase in activation with the K562 CD44v6 cells (both considering CD107 and TNF-α positivity).

This specific activation of CAR NK by the CD44v6 antigen is confirmed by the coculture of NK cells with the resistant MOLT-4 cell lines. A detectable activation, both as degranulation and TNF-α production, occurred only in CAR NK LNGFR+ cells (from both condition A and B), when incubated with MOLT-4 cells expressing the CD44v6 antigen.

Example 5—In Vivo Efficacy of NK and CAR-NK Cells 5.1 Experimental Design

The antitumour activity of CD44v6 CAR-NK cells was evaluated in an AIL xenogenic tumour model. The experiment consists in the infusion in NSG mice bearing THP1-leukaemia cells (minimal residual disease setting) NK cells, which were produced according to conditions described under examples 2 (transduction of cord blood derived stem cells under condition A or condition B) and example 3 (expansion and differentiation into CAR-NK cells or NK cells). The method including transduction under example 2 in condition B, followed by expansion and differentiation to NK cells under example 3, is a representative example of the method of the present invention.

Mice were infused at day 0 with THP1 cancer cells and three days later, were treated with adoptive immunotherapy.

The experiment includes seven experimental groups (Table 19)

TABLE 19

Experimental conditions

| Sample description | Glycostem Lot | MolMed references | Acronimous |
|---|---|---|---|
| PDE_M17112 A TRA | GSL25301527 | TRANSDUCED NK CONDITION A | A TR |
| PDE_M17112 B TRA | GSL25301529 | TRANSDUCED NK CONDITION B | B TR |
| PDE_M17112 A NT | GSL25301528 | NT CONTROL OF CONDITION A | A NT |
| PDE_M17112 B NT | GSL25301530 | NT CONTROL OF CONDITION B | B NT |
| Saline | n.a | TUMOUR ONLY | |

The experimental procedure is summarized in detail as indicated in Table 20

TABLE 20

Experimental procedure

| DAY | Process step |
|---|---|
| 0 | ➤ Intravenous Infusion of THP1 Cells in NSG mice tail (1.5 × $10^6$ cells/mouse) |
| 2 | ➤ Immunophenotype and viability of CAR NK and Mock NK cells |
| 3 | ➤ Immunophenotype and viability of CAR NK and Mock NK cells |
| | ➤ First infusion of NK cells and IL15 treatment (0.5 µg/mouse) |
| 6 | ➤ Immunophenotype and viability of CAR NK and Mock NK cells |
| | ➤ Second infusion of NK cells and IL15 treatment (0.5 µg/mouse) |
| | ➤ Medium change of NK cultured cells for third infusion |
| 9 | ➤ Immunophenotype and viability of CAR NK and Mock NK cells |
| | ➤ Third infusion of NK cells and IL 15 treatment (0.5 µg/mouse) |
| 12 | ➤ IL 15 treatment (0.5 µg/mouse) of NK infused mice |
| 15 | ➤ IL15 treatment (0.5 µg/mouse) of NK infused mice |
| 18 | ➤ IL15 treatment (0.5 µg/mouse) of NK infused mice |
| 39 | ➤ Liver analysis |

5.2 Materials
THP1 Tumour Cells

For in vivo efficacy experiments THP1 cell line, a human monocytic cell line derived from an acute monocytic leukaemia patient, was infused in mice to enable tumour engraftment. THP1 tumour cells were cultured and expanded for 12 days in RPMI+10% FBS, 100 U/ml Penicillin, 100 U/ml Streptomycin, 1 mM Sodium Pyruvate and 50 M beta mercaptoethanol. A total of 1.5E+06 cells/mouse were infused in tail vein at day 0.

Untransduced and CD44v6 CAR Transduced NIK cells (Condition A and B) 10 For the execution of the in vivo efficacy experiment, NIK cells cultured in different conditions (table 18) were produced, and kept in culture in basal culture medium (GBGM), supplemented with 200 human serum, a low dose cytokine cocktail containing 10 pg/ml GM-CSF, 250 pg/ml G-CSF and 50 pg/ml IL-6; 20 ng/ml SCF, IL-15, IL-7 and 1000 U/ml IL-2 (Proleukin), and infused in mice as indicated below (table 21).

TABLE 21

Total cells infused in mice

| | Condition A | | | Condition B | | |
|---|---|---|---|---|---|---|
| | Total | NK* | CAR-NK* | Total | NK* | CAR-NK* |
| Not Transduced | 74E+06 | 63.4E+06 | — | 53E+06 | 50E+06 | — |
| Transduced | 59E+06 | 53.5E+06 | 36.7E+06 | 48E+06 | 45.1E+06 | 8.5E+06 |

*The number of NK and CAR-NK positive cells was calculated on the basis of immunophenotype analysis; NK cells were defined as CD45+/CD56+/CD3−/7AAD−; CAR NK as CD271+/CD45+/CD56+/CD3−/7AAD−

NSG Mouse Model

NOD.Cg-Prkdcscid Il2rgtm1Wjl/SzJ (NSG) transgenic mice of 8 weeks of age were provided by Charles River Laboratories. Mice were infused at day 0 with 1.5E+06 THP1 cells for tumour engraftment. Two days after infusion, mice were randomized in five groups (five mice/group) from two different mice cohorts (male/female) and treated with the different cells preparation. NK cells and CAR NK from condition A (male cohort) and B (female cohort) were administered in sex-matched cohorts. NK cells were given at day 3-6-9 (1st, 2nd and 3rd infusion respectively). Control mice (male cohort) were left untreated. Recombinant hIL-15 (IL15) was provided as support at day 3-6-9-12-15-18.

Recombinant hIL-15 (IL15)

IL-15 (ImmunoTool) was reconstituted with sterile water at the concentration of 0.1 mg/ml, the solution and was aliquoted and frozen at −20° C.

(i) Methods

Immunophenotype and Viability

Cell viability was evaluated by counting cells with Trypan Blue staining solution. Cells were characterized for CD45-CD3-CD8-CD56-CD16-CD271 expression by FACS analysis. The population of CD56+ and CD56+CD271+ cells was determined by exclusion of 7AAD positive cells. The acquisition was performed on BD FACSCanto 2 and the data were analyzed using DIVA Software. Cells from condition A and B were analyzed at each day of infusion.

In Vivo THP1 and Therapeutic Cells Infusion

For in vivo efficacy experiments, THP1 tumour cells, NK cells and T cells were harvested, counted with Trypan Blue staining solution for cell viability and washed twice with PBS by centrifugation at 380 g for 10 minutes. Cells were resuspended in 0.9% saline solution at the desired concentration and infused in the mouse tail vein.

IL15 Treatment

IL15 was thawed and resuspended in 0.9% saline solution at the concentration of 5 µg/ml. Mice were treated with intraperitoneal injection of 0.5 pg of IL15 (100 µl/mouse) as indicated in the experimental procedure (Table 20).

Liver Excision

At day 39 mice were euthanized in C02 chamber according to ethical guidelines for animal experimentation. Livers were excised, weighted on analytical balance, data recorded, and images of excised livers were acquired.

5.4 Results

Figure 3:
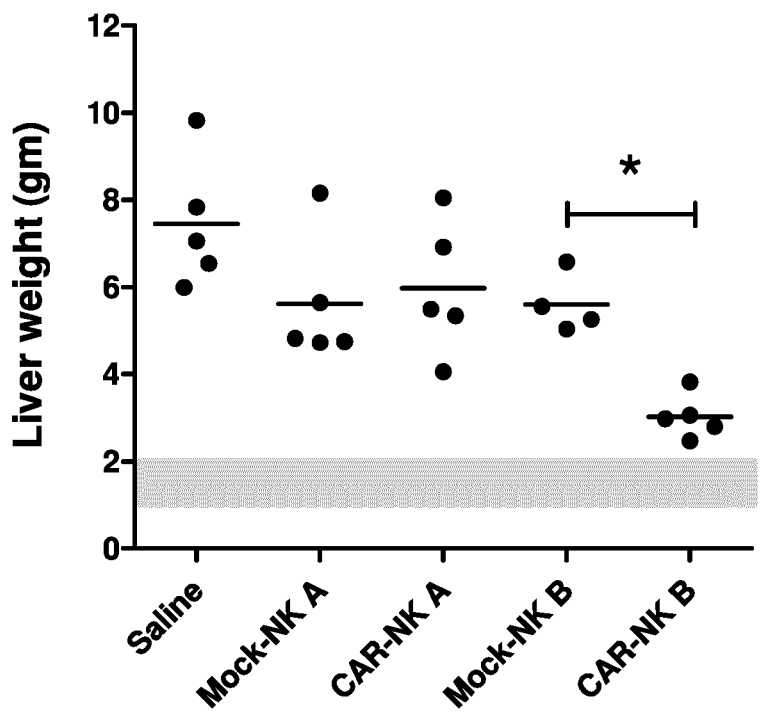
FIG. 3. In vivo antitumour effect of Mock NK and CD44v6 CAR-NK cells from Condition A and B in a well-established disease model. The figure shows liver weight (gram) for each condition. CD44v6 CAR-NK cells obtained under condition B i.e. according to the method of the invention results to have an antitumour effect stronger than controls.

In vivo antitumour effect of Mock NK and CD44v6 CAR-NK cells from Condition A and B were evaluated in a well-established disease model. FIG. 3 shows liver weight (gram) for each condition. Statistical analysis was performed with One Way Anova. CD44v6 CAR-NK cells obtained under condition B i.e. according to the method of the invention results to have an antitumour effect stronger than that obtained with Mock NK cells or with CD44v6 CAR-NK cells obtained under condition A.

Conclusions

In vivo results show that manufacturing method of the invention allows obtaining a cellular population characterized by a stronger antitumour effect as compared to untransduced NK cells as well as CAR-NK cells obtained with a process performed in different conditions. It results that the method of the present invention allows obtaining a cellular population containing CAR-NK cells characterized by the functional effect of both NK cells and of the CAR.

The invention claimed is:

1. A method for the manufacturing of a population of NK-cells, genetically modified with a Chimeric Antigen Receptor (CAR), the method comprising:
   (i) a first phase of production of an intermediate cellular population containing CD34+ cells carrying at least one polynucleotide coding for a CAR according to the following steps:
   a) obtaining a biological starting sample selected from the group consisting of bone marrow, peripheral blood, placenta material, or umbilical cord blood,
   b) isolating hematopoietic stem cells from such biological sample,
   c) obtaining a culture medium I by adding to a first basic culture medium a first collection of cytokines, wherein said first collection of cytokines comprises Interleukin-7 (IL-7), stem cell factor (SCF), flt-3Ligand (FLT-3L), thrombopoietin (TPO), granulocyte-macrophage-colony-stimulating factor (GM-CSF), granulocyte-colony-stimulating factor (G-CSF), and Interleukin-6 (IL-6),
   d) culturing the isolated hematopoietic stem cells in the presence of the culture medium I,
   e) transducing cultured stem cells by incubating such cells with a lentiviral vector carrying at least a polynucleotide coding for a CAR, thus obtaining an intermediate cellular population containing CAR-CD34+ stem cells, and
   f) culturing the intermediate cellular population containing CAR-CD34+ stem cells in the culture medium I for at least one day,
   (ii) a second phase comprising:
   g) obtaining a culture medium II by adding to a second basic culture medium a second collection of cytokines, wherein said second collection of cytokines comprises SCF, FLT-3L, Interleukin-15 (IL-15), IL-7, GM-CSF, G-CSF, and IL6,
   h) obtaining a culture medium III by adding to a third basic culture medium a third collection of cytokines, wherein said third collection of cytokines comprises SCF, IL-7, IL-15, Interleukin-2 (IL-2), GM-CSF, G-CSF, and IL-6,
   i) a step of further expanding the intermediate cellular population containing CAR-CD34+ stem cells from the first phase in the culture medium II, thereby obtaining a cellular population containing CAR-CD34+ stem cells and CAR-NK progenitor cells, and
   j) a step of expanding and differentiating the cellular population containing CAR-CD34+ stem cells and CAR-NK progenitor cells from step i) into a cellular population containing CAR-NK cells, the step comprising culturing the intermediate cellular population from phase I containing CAR-CD34+ stem cells or the cellular population from the optional preliminary step containing CAR-CD34+ stem cells and CAR-NK progenitor cells in the culture medium III, thereby obtaining a cellular population containing NK-cells.

2. The method according to claim 1, wherein the biological sample is umbilical cord blood.

3. The method according to claim 1, wherein stem cells are isolated using CD34+ immunomagnetic selection methods.

4. The method according to claim 1, wherein the transduction is performed in the culture medium I.

5. The method according to claim 1, wherein B the culture medium I includes SCF at concentration between 4 ng/ml and 300 ng/ml, FLT-3L B at concentration between 4 ng/ml and 300 ng/ml, TPO at concentration between 4 ng/ml and 100 ng/ml, and IL-7 at concentration between 4 ng/ml and 50 ng/ml of concentrations.

6. The method according to claim 1, wherein the phase of production of the intermediate cellular population includes one or more transduction runs.

7. The method according to claim 1, wherein CD34+ stem cells are incubated with a lentiviral vector at MOI between 10 and 200.

8. The method according to claim 7, wherein CD34+ stem cells are incubated with a lentiviral vector at MOI 100.

9. The method according to claim 1, wherein the lentiviral vector carries a further polynucleotide coding for a selectable protein for use as a marker for immune-selection.

10. The method according to claim 9 further comprising a step of selection of CAR-CD34+ stem cells using immune-magnetic selection methods.

11. The method according to claim 1, wherein the CAR contains a spacer domain for use as a marker for immune-selection.

12. The method according to claim 11 further comprising a step of selection of CAR-CD34+ stem cells using immune-magnetic selection methods.

* * * * *